(12) United States Patent
Hirota et al.

(10) Patent No.: US 6,465,190 B1
(45) Date of Patent: Oct. 15, 2002

(54) METHOD FOR PRODUCING DNA CHIP

(75) Inventors: Toshikazu Hirota; Nobuo Takahashi, both of Owariasahi; Yukihisa Takeuchi; Takao Ohnishi, both of Aichi, all of (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 09/694,135

(22) Filed: Oct. 23, 2000

(30) Foreign Application Priority Data

Oct. 22, 1999 (JP) ............................................. 11-301627
Mar. 13, 2000 (JP) ......................................... 2000-069285

(51) Int. Cl.[7] ........................... C12Q 1/68; C12P 19/34; C07H 19/00; G01N 15/06
(52) U.S. Cl. ......................... 435/6; 435/91.1; 435/91.2; 536/22.1; 422/50; 422/68.1
(58) Field of Search ........................... 435/6, 91.1, 91.2; 536/22.1; 422/50, 68.1

(56) References Cited

U.S. PATENT DOCUMENTS

| | | |
|---|---|---|
| 4,649,121 A | 3/1987 | Ismail et al. .................. 436/14 |
| 4,877,745 A | 10/1989 | Hayes et al. ................... 436/16 |
| 6,150,103 A | * 11/2000 | Ness et al. ...................... 435/6 |

FOREIGN PATENT DOCUMENTS

| | | |
|---|---|---|
| CA | 1101771 | 5/1981 |
| EP | 0119573 | 9/1984 |
| JP | 6-040030 A | 2/1994 |
| JP | 8-201265 A | 8/1996 |
| WO | 84/03151 | 8/1984 |

* cited by examiner

Primary Examiner—Jezia Riley
(74) Attorney, Agent, or Firm—Burr & Brown

(57) ABSTRACT

Disclosed is a method comprising a pretreatment step of forming a poly-L-lysine layer on a surface of a base plate, a sample preparation step of preparing a sample containing a DNA fragment, a dilution step of diluting the concentration of the obtained sample, and a supply step of supplying a diluted sample solution onto the base plate to produce a DNA chip. The sample preparation step includes an amplification step of PCR-amplifying the DNA fragment to prepare a PCR product, a powder formation step of drying the obtained PCR product to form DNA powder, and a mixing step of dissolving the obtained DNA powder in a buffer solution.

39 Claims, 16 Drawing Sheets

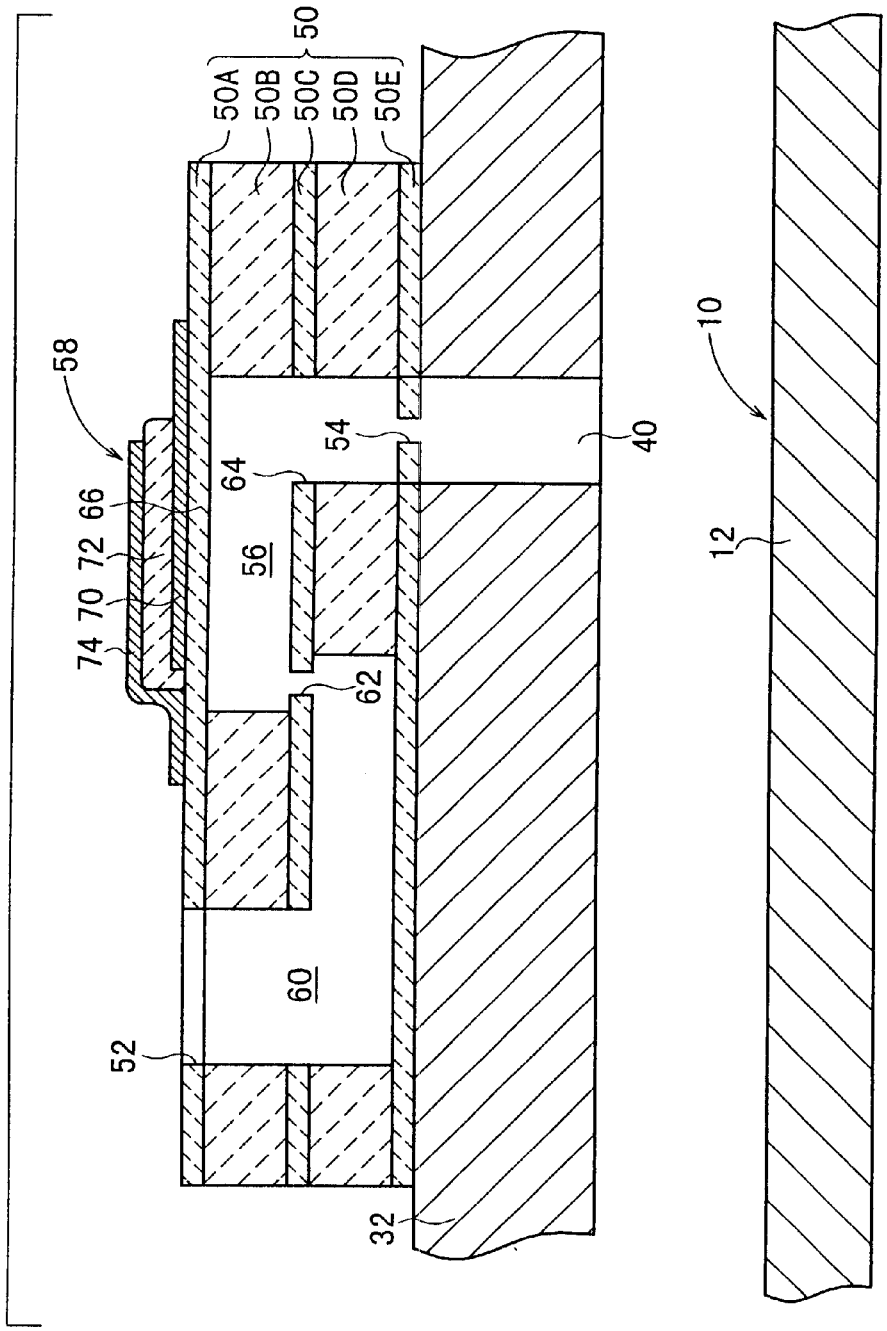

METHOD FOR PRODUCING DNA CHIP

BACKGROUND OF THE INVENTION

1. Field of the Invention

The present invention relates to a method for producing a DNA chip (DNA microarray) in which several thousands to not less than ten thousands kinds of different types of DNA fragments are aligned and fixed as spots at a high density on a base plate such as a microscopic slide glass.

2. Description of the Related Art

The method for analyzing the genetic structure has been remarkably progressed in recent years. A large number of genetic structures represented by those of human gene have been clarified. The analysis of the genetic structure as described above uses a DNA chip (DNA microarray) in which several thousands to not less than ten thousands kinds of different types of DNA fragments are aligned and fixed as spots on a base plate such as a microscopic slide glass.

Those widely used as a method for forming the spots during the production of the DNA chip are based on a system such as the QUILL system, the pin & ring system, and the spring pin system in which a sample solution containing DNA fragments is supplied (stamped) onto the base plate by using a so-called pin. Even when any one of the foregoing methods is adopted, it is necessary to suppress the dispersion of the volume and the shape of each of the spots to be low so that the distance between the respective spots is maintained to be constant.

On the other hand, in order to realize a higher density, it is also greatly expected to develop a new method in which the shape control performance is satisfactory for the spot, and the productivity is excellent.

As shown in FIG. 16, when a spot is formed by dripping a sample solution onto a base plate 200, the spot is hemispherical in accordance with the surface tension. In this procedure, a substantial amount of the sample immobilized on the base plate 200 resides in a slight portion 204 contacting with the base plate 200. The amount is merely a part of the whole (spherical matter). The remaining portion 206 is not immobilized, and hence it is washed away during the washing step performed thereafter. As a result, a problem arises that a large amount of the sample solution is lost, and the efficiency of the use of the sample solution is low.

The cost for the production of the DNA chip is substantially determined by the amount of the sample solution. In the case of the procedure described above, almost all of the sample solution is washed away, and the procedure is disadvantageous in view of the production efficiency.

Several thousands to not less than ten thousands kinds of different types of sample solutions are dripped onto one base plate. However, the viscosity and the surface tension differ for each of the different types of the sample solutions. Therefore, in order to obtain an identical spot diameter, it is necessary to change the dripping amount of the sample solution depending on, for example, the viscosity and the surface tension.

However, in the case of the conventional technique, the sample solution adhered to a pin is allowed to physically make contact with the base plate together with the pin so that the sample solution is dripped. Therefore, the spot is formed on the base plate by means of one time of tripping. As a result, the following problem arises. That is, it is impossible to perform any delicate control of the dripping (control of the dripping amount and the dripping position), and any dispersion occurs in the spot diameter formed on the base plate.

In order to more reliably immobilize the DNA fragment in the sample solution onto the base plate, a method has been also developed, in which an organic or inorganic polymer is mixed in the sample solution to physically hold the DNA fragment in the polymer cross-link. However, in the case of this procedure, the following problem arises. That is, the viscosity of the sample solution is increased, and the sample solution tends to be dried, thickened, and solidified. The pot life of the sample upon the formation of the spot is shortened, and the amount of one time of dripping is increased.

SUMMARY OF THE INVENTION

The present invention has been made taking the foregoing problems into consideration, an object of which is to provide a method for producing a DNA chip, which makes it possible to improve the efficiency of the use of an expensive sample solution, improve the productivity of the DNA chip, and improve the yield.

Another object of the present invention is to provide a method for producing a DNA chip, which makes it possible to control the supply depending on the type of a sample solution supplied onto a base plate, realize a uniform spot diameter formed on the base plate, and improve the reliability and the quality of the DNA chip.

According to the present invention, there is provided a method for producing DNA chip including a large number of spots of sample solutions arranged on a base plate, the method comprising the step of supplying the sample solutions onto the base plate; wherein the sample solution is supplied a plurality of times to form one of the spots.

Accordingly, it is possible to improve the yield of the DNA chip. In this process, it is preferable that the sample solution is supplied by an ink-jet system.

When the ink-jet system is used, a large number of liquid droplets in a required amount can be supplied onto the base plate at a high speed (to 100 kHz) in a manner to make no contact with the base plate. The supply source is continuously supplied via a pouring port and a cavity connected to a discharge port for discharging the liquid droplets. Therefore, unlike the conventional pin system, it is unnecessary to move the pin to a supply source (sample well) for the sample solution to immerse the pin tip in the sample solution every time the spot is formed. Thus, it is possible to form the spots on a large number of base plates for a short period of time.

It is preferable that the sample solution is obtained by diluting a sample containing a DNA fragment to give a predetermined concentration. In this process, it is preferable that the sample solution is obtained by diluting the sample containing the DNA fragment with water or an aqueous solution containing sodium chloride or an aqueous solution containing a polymer. It is preferable that the sample solution is diluted to give a concentration of such a degree that final desired base pairs per one spot are satisfied, by performing the supply a plurality of times to form one of the spots.

The following advantage is obtained by diluting the concentration of the sample. That is, it is possible to relatively decrease the amount of the expensive DNA fragment in the sample solution adhered or remained in the supply flow passage path at the stage at which the supply of the sample solution onto the base plate comes to an end. The following effect is also obtained. That is, it is possible to avoid the occurrence of any defect which would be otherwise caused such that the solution is dried, thickened, and solidified due to the concentrated sample solution, and the discharge port is clogged to cause defective discharge. A greater advantage is obtained that when the sample solution is supplied onto the base plate, then the sample solution becomes not hemispherical but flat. In this case, almost all of the sample solution supplied to the base plate is immobilized on the base plate. Therefore, most of the sample solution is not washed away during the washing step to be performed thereafter. Thus, it is possible to improve the efficiency of the use of the sample solution.

Further, it is possible to realize a uniform spot diameter of the sample solution formed on the base plate, by changing the degree of the dilution depending on the type of the DNA fragment contained in the sample solution so that the viscosity and the surface tension of the sample solution are varied.

Further, it is preferable that the sample solution is diluted with the aqueous solution containing the polymer. Accordingly, the shape-retaining performance is increased for the spot shape after being supplied onto the base plate. The shape is stabilized, and it is possible to avoid any change of the shape which would be otherwise caused by drying and contraction of the spot.

As described above, according to the present invention, it is possible to improve the efficiency of the use of the sample solution of the expensive cost, and it is possible to improve the productivity of the DNA chip and improve the yield. The dripping control can be performed depending on the type of the sample solution to be dripped. It is possible to realize the uniform spot diameter formed on the base plate. It is possible to improve the reliability and the quality of the DNA chip.

In the production method described above, the sample is prepared by carrying out the steps of PCR-amplifying the DNA fragment to prepare a PCR product; drying the PCR product to obtain DNA powder; and dissolving the DNA powder in a buffer solution. The sample as described above undergoes no change in quality, and it is well dispersed in the aqueous solution, when the sample is diluted. The sample is suitable for the dilution, and the concentration can be correctly managed upon the dilution.

In the production method described above, it is also preferable that a dispenser is used when the sample solution is supplied onto the base plate, the dispenser comprising a plurality of arranged micropipettes each including a pouring port for pouring the sample solution from the outside, a cavity for pouring and charging the sample solution thereinto, and a discharge port for discharging the sample solution, formed on at least one or more substrates, the micropipette further including a piezoelectric/electrostrictive element disposed on at least one wall surface of the substrate which forms the cavity so that the sample solution is movable in the cavity, and mutually different types of the sample solutions being discharged from the discharge ports of the respective micropipettes.

Every time the piezoelectric/electrostrictive element is driven, then a minute amount of the liquid is discharged from the discharge port, and the volume thereof is minute and constant without involving dispersion. The driving cycle can respond to the high frequency wave by using the piezoelectric/electrostrictive element. The time required for the discharge is shortened as well. The sample solution is moved in the closed space from the pouring of the sample solution to the discharge. Therefore, the sample solution is not dried during any intermediate process. Further, the entire substrate can be formed to be small and compact. Therefore, it is possible to shorten the flow passage through which the sample solution is moved. Accordingly, it is possible to suppress the problem of adhesion of the sample solution to the flow passage wall to be minimum, and it is possible to avoid the deterioration of the efficiency of the use of the sample solution.

It is also preferable that a dispenser is used when the sample solution is supplied onto the base plate, the dispenser comprising a plurality of arranged micropipettes each including a pouring port for pouring the sample solution from the outside, a cavity for pouring and charging the sample solution thereinto, and a discharge port for discharging the sample solution, formed on at least one or more substrates, so that the sample solution is movable in the cavity, and the sample solution of an identical type is discharged from at least two or more of the discharge ports to form one spot.

When the sample solution of the identical type is discharge from two or more of the discharge ports to form one spot, then it is possible to more quicken the speed for forming the spot, and it is possible to improve the throughput.

In general, when the sample solution is supplied a plurality of times, the spot diameter is increased every time the supply is performed. However, the number of times of supply can be increased without increasing the spot diameter by delaying (increasing) the supply interval, or applying a treatment so that the sample solution supplied onto the base plate is quickly dried, thickened, and solidified as described later on.

When the supply interval is increased, then the sample solution, which is disposed at the portion of the discharge port opened toward the discharge side, is dried to some extent before the discharge, and the sample solution is discharged in a state in which the viscosity is increased, i.e., in a so-called semidried state. Therefore, the spot diameter is not increased even when the supply is repeated. However, in this method, the time required to form the spot is consequently increased, which is not preferred. In such a case, there are a lot of limitations to periodically manage the so-called semidried state, and the nozzle of defective discharge is apt to appear.

Accordingly, when the sample solution of the identical type is discharged from the two or more discharge ports to form one spot, two or more discharge ports, at which the sample solution is progressively dried at the portion of the discharge port opened toward the discharge side, exist during the period in which the discharge port is moved to the discharge position, i.e., during the waiting period until the discharge is started. The identical sample solution can be supplied by using the discharge ports as described above. As a result, it is possible to shorten the time required to form the spot.

If the nozzle of defective discharge appears by any chance, it is possible to prevent the loss of the expensive sample solution beforehand, by discharging with the indefective nozzle. Further, it is preferable to use a structure in which one pouring port communicates with the cavity connected with at least two or more of the discharge ports for discharging the sample solution of the identical type, because it is possible to reduce the number of times of the pouring operations for the sample solution.

It is also preferable that the sample solution of the identical type is discharged at the substantially simultaneous timing from at least two or more of the discharge ports, in the case of using the non-contact ink-jet system. In this case, it is also preferable that the falling points are allowed to coincide with each other for the sample solution to be discharged. By doing so, it is possible to improve the speed for forming the spot.

However, in order to obtain a higher accuracy for the position accuracy of the sample solution to be supplied onto the base plate, it is preferable to use a method in which the sample is supplied at deviated discharge timings when each of the discharge ports is located just over the spot formation position.

It is preferable that the plurality of micropipettes, each of which is constructed such that the sample solution is moved in the cavity in a laminar flow, are arranged. When the sample solution is moved in the form of laminar flow, it is possible to avoid the occurrence of bubble or the like, and it is possible to avoid the defective discharge. Thus, the durability of the micropipette is increased.

It is preferable when the dispenser is used; then mutually different types of the sample solutions are poured into the plurality of cavities from the pouring ports corresponding to the discharge ports for discharging the mutually different types of the sample solutions, and then the different types of the sample solutions in the plurality of cavities are discharged from the discharge ports by driving the piezoelectric/electrostrictive elements. According to the arrangement as described above, the plurality of different types of the sample solutions can be supplied onto the base plate at the same timing without causing any cross-contamination.

It is also preferable that when the dispenser is used; a substitution solution is previously charged into the plurality of cavities, different types of the sample solutions are subsequently poured from the pouring ports while effecting substitution in the plurality of cavities, and then the piezoelectric/electrostrictive elements are driven so that the different types of the sample solutions in the plurality of cavities are discharged from the discharge ports. The occurrence of the defective discharge can be completely avoided, and the expensive sample can be efficiently discharged by previously substituting the interior of the cavity with the inexpensive substitution solution, and then effecting the substitution with the expensive sample.

The substitution from the substitution solution to the sample solution in the cavity may be performed by aspirating and discharging the substitution solution from the discharge port, for example, by means of the vacuum suction. However, it is preferable that the different types of the sample solutions are poured from the pouring ports while effecting the substitution in the plurality of cavities, while driving the piezoelectric/electrostrictive elements. By doing so, the amount of the substitution solution to be discharged can be accurately controlled, without involving any loss of the discharge of the expensive sample solution.

The end point of the completion of the substitution may be controlled, for example, by the substitution time and the discharge amount by previously determining the volume and the movement speed of the sample. However, it is more preferable that the end point of the completion of the substitution is recognized by sensing the change of the fluid characteristic in the concerning cavity, because the end point can be detected more accurately.

In the present invention, the completion of the substitution is recognized by sensing the change of the fluid characteristic in the cavity. Therefore, even when the sample solution and the substitution solution are mixed with each other to some extent in the flow passage, the mixed portion can be easily distinguished from the unmixed portion to make accurate judgement. As a result, it is possible to decrease the amount of the sample solution which should be purged by being mixed with the substitution solution. Thus, it is possible to increase the efficiency of the use of the sample solution.

The change of the fluid characteristic in the cavity may be recognized by applying a voltage to the piezoelectric/electrostrictive element to excite vibration, and detecting the change of the electric constant caused by the vibration. Accordingly, it is unnecessary to install, for example, any special detecting element. The detection can be performed inexpensively and accurately.

It is preferable that the substitution solution is previously subjected to a degassing treatment. By doing so, the substitution solution can be smoothly charged into the cavity without generating any bubble or the like and without causing any clogging during the process. Accordingly, the substitution into the sample solution is reliably performed, and the discharge is stabilized. Further, it is also preferable that the substitution solution is poured and charged into the cavities, an intermediate solution containing no DNA fragment, which has approximately the same specific gravity as that of the sample solution, is subsequently poured from the pouring ports to effect substitution in the cavities, the different types of the sample solutions are subsequently poured from the pouring ports into the cavities, and thus the sample solution are charged. The inexpensive intermediate solution containing no DNA fragment, which has approximately the same specific gravity as that of the sample solution, is allowed to intervene between the substitution solution and the sample solution. Accordingly, it is possible to avoid an inconvenience which would be otherwise caused such that the expensive sample solution is mixed with the substitution solution having the different specific gravity, and consequently the purge amount is inevitably increased.

In the present invention, the plurality of micropipettes are used. Therefore, many kinds of samples can be simultaneously supplied at once. Further, any pipette, in which any partial defect occurs, can be exchanged with ease. Therefore, it is easy to perform the maintenance. Further, the discharge ports are aligned and arranged two-dimensionally. Therefore, for example, this arrangement is optimum when the spots are aligned and fixed two-dimensionally on the base plate.

In the present invention, it is preferable that when the sample solution is supplied onto the base plate, the sample solution is supplied while drying, thickening, or solidifying at least the sample solution. Accordingly, the immobilization of the sample solution supplied onto the base plate is quickened. It is possible to effectively avoid any weakening (phenomenon in which the spot diameter is expanded) associated with the dilution of the sample solution.

It is exemplified that the treatment of drying, thickening, or solidifying the sample solution is, for example, to heat the base plate, and to heat the discharged or supplied sample solution. It is preferable to use, for example, a laser beam, an infrared ray, and an electromagnetic wave, as a heating method.

The methods as described above especially make it possible to selectively heat a minute region. As in the present invention, it is necessary that the spot of the discharged sample solution is quickly heated, while it is necessary to avoid the occurrence of the defective discharge due to the drying or the like caused by the heating at the discharge port disposed just closely to the spot. In such a situation, it is preferable to use the treatment of drying, thickening, or solidifying the sample solution as described above. Especially, the electromagnetic wave can be reliably cut off by means of a metal shield. Therefore, the electromagnetic wave is preferred in order to avoid any unnecessary heating of the discharge port. When the laser beam or the infrared ray is used, the laser beam or the infrared ray is radiated onto the base plate to indirectly heat the sample solution.

In the present invention, it is also preferable that a treatment of drying, thickening, or solidifying the dripping sample solution is to cool the base plate or the discharged or supplied sample solution. The cooling procedure is preferably adopted when DNA in the sample solution is damaged by the heating or when any component in the sample solution is softened by the heating.

In the present invention, it is also preferable that when the sample solution is supplied onto the base plate, the sample solution is supplied while deviating a supply position, or the sample solution is supplied while changing a supply amount. That is, for example, the sample solution is supplied to mutually different positions two times to one hundred times to form one spot diameter depending on the type of the sample solution. In this procedure, the number of supply operations can be changed depending on the type of the sample solution, and the supply position can be determined. Therefore, all of the spot diameters can be formed to be uniform, irrelevant to the type of the sample solution. Thus, it is possible to improve the DNA chip and improve the reliability.

The formation of one spot while deviating the supply position cannot be performed by using the conventional pin system spotting. The technique as described above can be firstly realized in accordance with the ink-jet system in which the supply amount per one droplet is about $1/100$ to $1/10$ as compared with the pin system. When the technique is combined with the treatment of drying, thickening, or solidifying the sample solution, it is possible to realize a spot shape other than the conventional circular shpt shape. An advantage is obtained such that it is possible to widen the range capable of effecting the matching with a DNA chip reader (for example, a CCD image pickup device).

Further, the formation of one spot while deviating the supply position with minute droplets also makes it possible to control the shape of the spot in the height direction by adjusting the stacking position thereof. An advantage is obtained such that the fluorescence intensity pattern emitted from the spot can be freely designed in the spot.

The supply amount can be changed by changing the number of supply operations, as well as by changing the discharge condition, i.e., the voltage pattern applied to the piezoelectric/electrostrictive element in the case of the ink-jet system.

In the present invention, it is preferable that vibration is applied to the sample solution during the supply or prior to the supply of the sample solution onto the base plate.

In this procedure, it is possible to avoid any precipitation of the DNA fragment contained in the sample solution. It is possible to uniformly disperse the DNA fragment in the sample solution. Accordingly, it is possible to almost exclude the dispersion of the content of the DNA fragment for the same types of the sample solutions to be formed on the respective base plates. It is possible to exclude the dispersion in the genetic analysis for every base plate.

According to another aspect of the present invention, there is provided a method for producing a DNA chip including a large number of spots of sample solutions arranged on a base plate, the method comprising the step of supplying the sample solutions onto the base plate in accordance with an ink-jet system; wherein when the sample solution is supplied onto the base plate, a humidity around a portion to which the sample solution is discharged and supplied is selectively increased as compared with those around the other portions so that the sample solution is not dried, thickened, or solidified. Accordingly, especially when the sample solution, which tends to be dried, thickened, or solidified, is used, it is possible to avoid any defective discharge.

In the present invention, it is also preferable to adopt the steps of cooling the base plate to be not more than 0° C. after preparing the base plate on which the large number of spots are arranged by supplying the sample solutions onto the base plate, and then returning the base plate in an atmosphere at room temperature in which a sufficient volume of gas exists at a humidity of not less than 30%.

It is also preferable that the base plate is exposed in an atmosphere in which a sufficient volume of gas exists at a humidity of not less than 80%, or to water vapor containing mist, after preparing the base plate on which the large number of spots are arranged by supplying the sample solutions onto the base plate.

The inventions described above are preferably adopted when the sample solution, in which a polymer or the like is mixed to increase the viscosity, is used, the dripping method for the sample solution is adjusted, and the shape of the spot on the base plate exhibits, for example, a so-called doughnut-shaped configuration in which the circumferential edge portion is bulged, and the central portion is recessed.

In the case of the doughnut-shaped configuration as described above, the boundary between the base plate and the circumferential edge portion of the spot is conspicuous, and it is easily observed. When the spot of the colorless and transparent liquid such as the sample solution containing the DNA fragment is formed, for example, on the colorless and transparent glass base plate, the following advantage is obtained. That is, it is easy to observe the shape of the spot, and it is easy to inspect whether the shape of the spot is satisfactory or defective.

However, in the case of the spot having the doughnut-shaped configuration as described above, the substantial immobilized sample is plentiful (thick) at the circumferential edge portion, even when most of the bulged portion at the circumferential edge is washed away in the washing step during the immobilization to be performed thereafter. Therefore, in the case of the use as the DNA chip, the distribution of fluorescence emission amount emitted from the spot exhibits a doughnut-shaped configuration in the spot, consequently causing a factor to bring about the dispersion and the deterioration of the sensitivity.

Therefore, in order to realize both of the easy inspection (doughnut-shaped configuration) and the good shape of the spot (non-doughnut-shaped configuration), the following method is appropriate. That is, when the sample solution is supplied onto the base plate, the discharge is performed in accordance with the ink-jet system or the like to drip the sample solution onto the base plate so that the sample solution is concentrated at the circumferential edge portion of the spot by controlling the kinetic energy and the hydrophobic property with respect to the base plate to form the doughnut-shaped configuration. After that, the viscosity of the sample solution is previously increased to such an extent that the spot is not spherical against the surface tension of the liquid, while the fluidity of the sample solution to form the spot is increased after completion of the inspection so that the doughnut-shaped configuration is changed to the non-doughnut-shaped configuration by the aid of the surface tension. The present invention is preferred in order to realize the method described above.

That is, the base plate, on which the spot having the doughnut-shaped configuration is formed, is cooled to be not more than 0° C. and then the base plate is returned in the atmosphere at room temperature in which the sufficient volume of gas exists at the humidity of not less than 30%.

Alternatively, the base plate is exposed in the atmosphere in which the sufficient volume of gas exists at the humidity of not less than 80%, or to the water vapor containing the mist. By doing so, the water is incorporated into the sample solution from the surrounding gas, or the mist makes contact to increase the fluidity of the sample solution. Accordingly, the shape of the spot is changed to a hemispherical configuration which is the non-doughnut-shaped configuration. Thus, it is possible to improve the sensitivity of the DNA chip and reduce the dispersion of the sensitivity. Of course, after the shape of the spot is hemispherical, the base plate may be immediately introduced into the drying step to fix the shape. It is a matter of course that when the base plate is exposed to the water vapor, it is necessary that the temperature of the water vapor is not more than a temperature of such an extent that the DNA fragment is not denatured.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 5 shows a longitudinal sectional view illustrating an arrangement of the micropipette;

DESCRIPTION OF THE PREFERRED EMBODIMENTS

Several exemplary embodiments of the method for producing the DNA chip according to the present invention will be explained below with reference to FIGS. 1 to 15.

Figure 1:
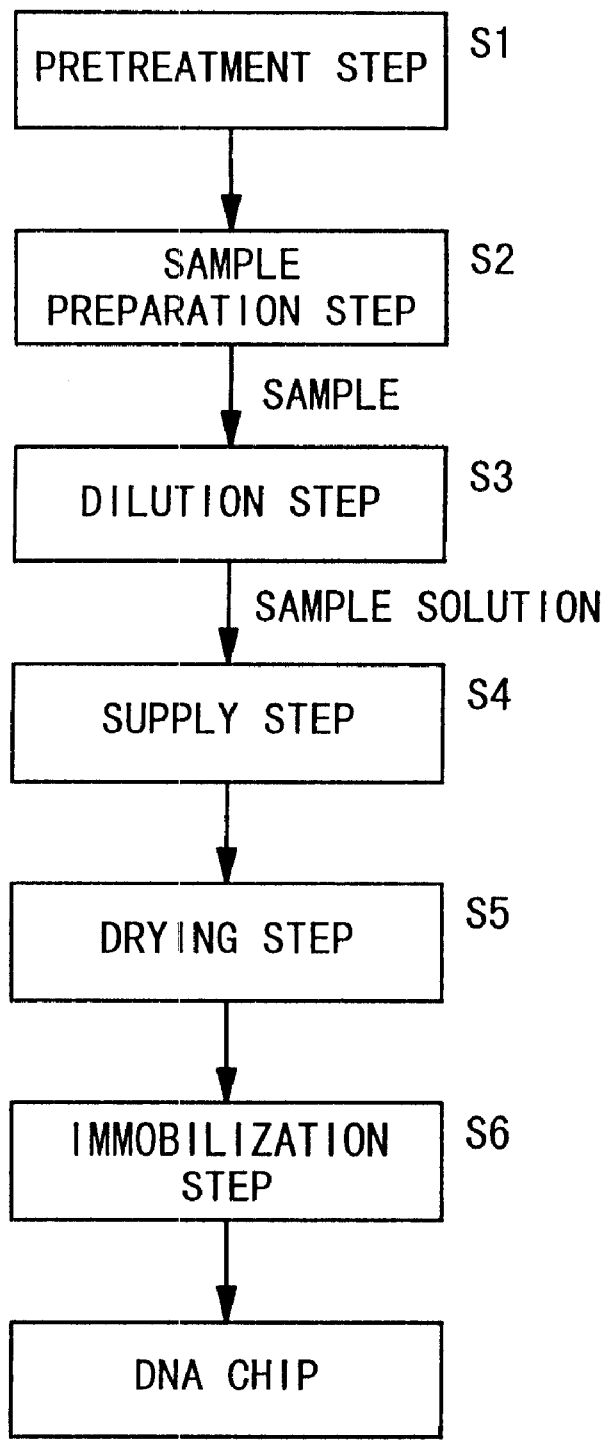
FIG. 1 shows a block diagram illustrating the steps of a method for producing a DNA chip according to an embodiment of the present invention.
Figure 3:
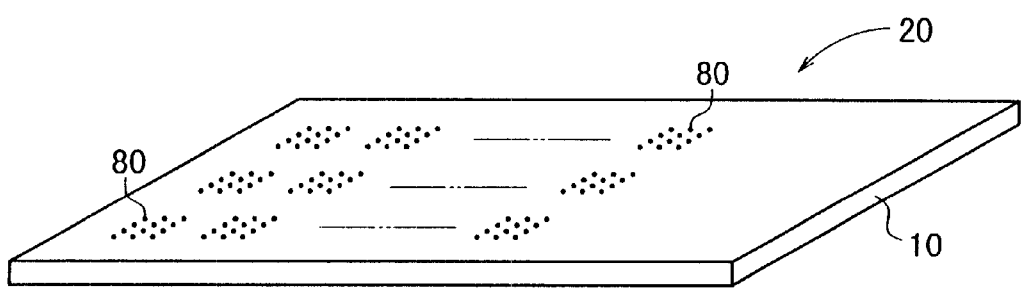
FIG. 3 shows a perspective view illustrating the DNA chip to be produced.

As shown in FIG. 1, a method for producing a DNA chip according to an embodiment of the present invention comprises a pretreatment step S1 for forming a poly-L-lysine layer 12 on a surface of a base plate 10 (see FIG. 10A), a sample preparation step S2 for preparing a sample containing a DNA fragment, a dilution step S3 for diluting the concentration of the obtained sample, a supply step S4 for supplying (including dripping) a diluted sample solution onto the base plate 10 to prepare the spotted base plate including a large number of spots 80 arranged on the base plate 10 as shown in FIG. 3, a drying step S5 for applying heat to the base plate 10 to dry the spots 80, and an immobilization step S6 for immobilizing the DNA fragments in the spots 80 on the base plate 10 to produce the DNA chip 20 shown in FIG. 3.

Figure 2:
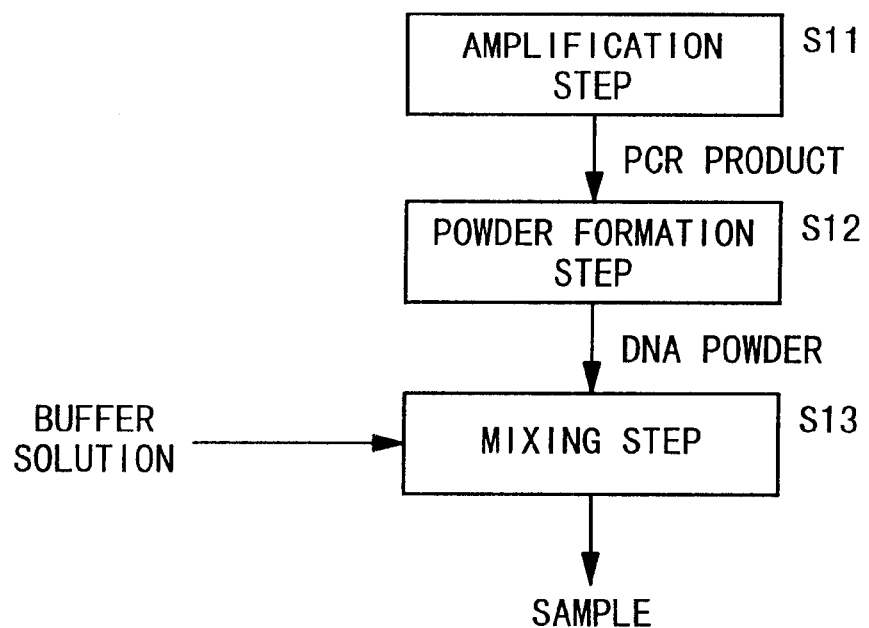
FIG. 2 shows block diagram illustrating details of the step of sample preparation.

As shown in FIG. 2, the sample preparation step S2 includes an amplification step S1 for PCR-amplifying the DNA fragment to prepare a PCR product, a powder formation step S12 for drying the obtained PCR product to form DNA powder, and a mixing step S13 for dissolving the obtained DNA powder in a buffer solution.

The steps will be specifically explained below. In the pretreatment step S1, at first, the base plate 10 is immersed in an alkaline solution, followed by being gently shaken for at least 2 hours at room temperature. The alkaline solution is one obtained, for example, by dissolving NaOH in distilled water and adding ethanol thereto, followed by being agitated until the solution is completely transparent.

After that, the base plate 10 is taken out, and it is transferred into distilled water, followed by being rinsed to remove the alkaline solution. Subsequently, the base plate 10 is immersed in a poly-L-lysine solution prepared by adding poly-L-lysine to distilled water, followed by being left to stand for 1 hour.

After that, the base plate 10 is taken out, and it is applied to a centrifugal machine to perform centrifugation so that any excessive poly-L-lysine solution is removed. Subsequently, the base plate 10 is dried at 40° C. for about 5 minutes to obtain the base plate 10 comprising the poly-L-lysine layer 12 formed on the surface.

Subsequently, in the sample preparation step S2, at first, 3 M sodium acetate and isopropanol are added to the PCR product amplified with a known PCR equipment (amplification step S11), followed by being left to stand for several hours. After that, the PCR product solution is centrifuged with a centrifugal machine to precipitate the DNA fragment.

The precipitated DNA fragment is rinsed with ethanol, and it is centrifuged, followed by being dried to produce the DNA powder (powder formation step S12). A buffer solution (for example, TE buffer solution) is added to the obtained DNA powder, followed by being left to stand for several hours to completely dissolve the DNA powder (mixing step S13). Thus, the sample solution is prepared. At this stage, the concentration of the sample is 1 to 10 $\mu g/\mu l$.

In this embodiment, the concentration of the obtained sample is diluted (dilution step S3). In the dilution step S3, the sample is diluted by using, for example, water, an aqueous solution containing sodium chloride, or an aqueous solution containing a polymer. The sample solution after the dilution may be left to stand for 1 hour to several hours, if necessary. Alternatively, the sample solution after the dilution may be subjected to mixing based on refrigeration-thawing so that the sample and the dilution solution are adapted to one another. After that, the diluted sample solution is centrifuged, or it is subjected to a vacuum defoaming treatment to remove any bubble in the solution. The sample solutions are supplied onto the base plate 10 to prepare the spotted substrate (supply step S4).

Especially, in this embodiment, a dispenser 30 as shown in FIGS. 4A to 4C and FIG. 5 is used for the supply step S4.

The dispenser 30 includes, for example, ten micropipettes 34 which are arranged in five rows and two columns on the upper surface of a fixation plate 32 having a rectangular configuration. A group of the micropipettes 34, which are aligned in the direction of the respective columns, are fixed on the fixation plate 32 by the aid of a fixing jig 36 respectively.

Figure 4A:
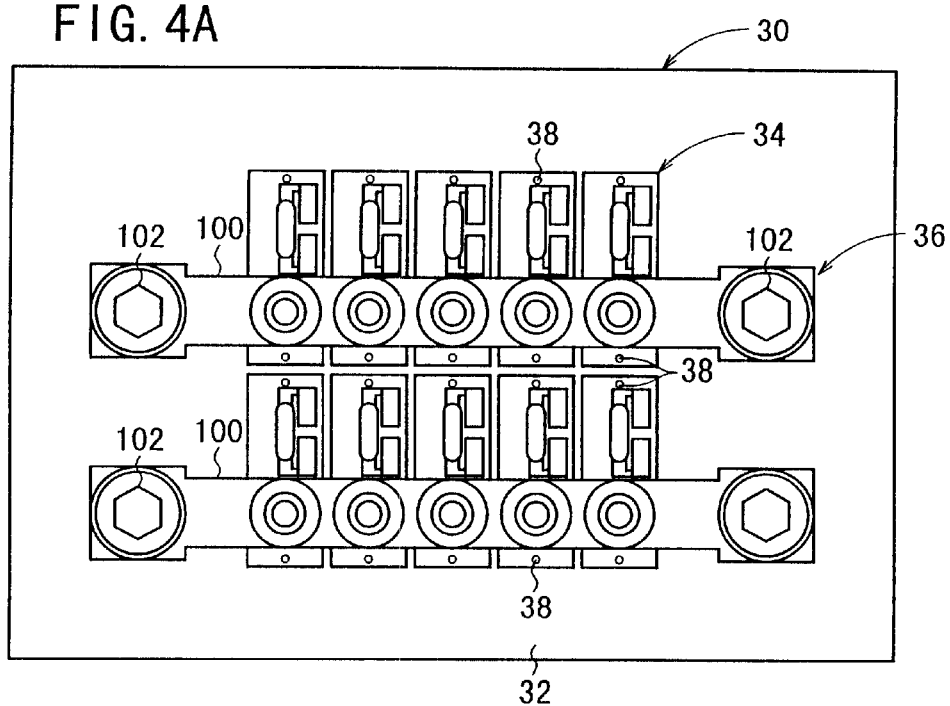
FIG. 4A shows a plan view illustrating an arrangement of a dispenser to be used for the method for producing the DNA chip according to the embodiment of the present invention.
Figure 4B:
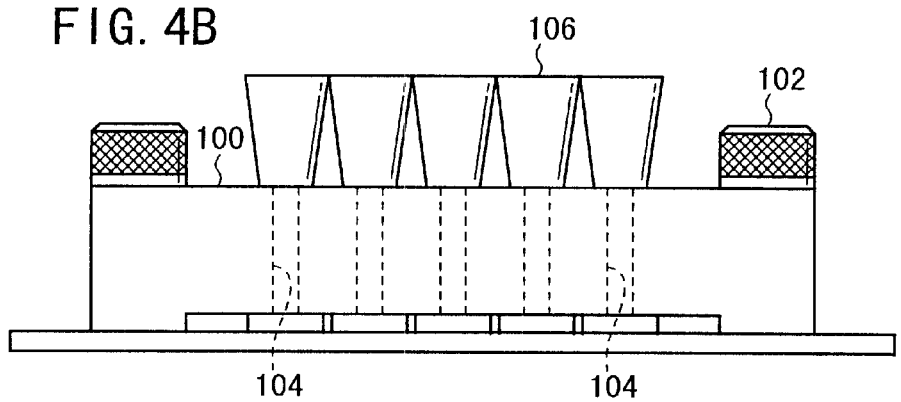
FIG. 4B shows a front view thereof.
Figure 4C:
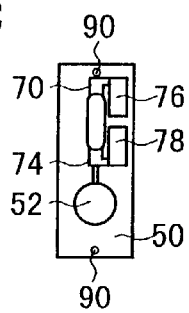
FIG. 4C shows a magnified plan view illustrating one micropipette for constructing the dispenser.

As shown in FIGS. 4C and 5, the micropipette 34 comprises a sample-pouring port 52 which is formed at the upper surface of a substrate 50 having a substantially rectangular parallelepiped-shaped configuration, a sample discharge port 54 which is formed at the lower surface of the substrate 50, a cavity 56 which is formed at the inside between the sample-pouring port 52 and the sample discharge port 54, and an actuator section 58 which is used to vibrate the substrate 50 or change the volume of the cavity 56.

Therefore, as shown in FIG. 2, through-holes 40 are provided through the fixation plate 32 at portions corresponding to the sample discharge ports 54 of the micropipettes 34 respectively. Accordingly, the sample solution, which is discharged from the sample discharge port 54 of the micropipette 34, is supplied (or dropped) through the through-hole 40, for example, to the base plate 10 which is fixed under the fixation plate 32.

An introducing bore 60 having a substantially L-shaped configuration with a large opening is formed over a region ranging from the sample-pouring port 52 to the inside of the substrate 50 in the micropipette 34. A first communication hole 62 having a small diameter is formed between the introducing bore 60 and the cavity 56. The sample solution, which is poured from the sample-pouring port 52, is introduced into the cavity 56 through the introducing bore 60 and the first communication hole 62.

A second communication hole 64, which communicates with the sample discharge port 54 and which has a diameter larger than that of the first communication hole 62, is formed at a position different from that of the first communication hole 62, of the cavity 56. In the embodiment of the present invention, the first communication hole 62 is formed at the portion of the lower surface of the cavity 56 deviated toward the sample-pouring port 52. The second communication hole 64 is formed at the position of the lower surface of the cavity 56 as well corresponding to the sample discharge port 54.

Further, in this embodiment, the portion of the substrate 50, which is the upper surface of the cavity 56, is thin-walled to give a structure which tends to undergo the vibration of the external stress so that the portion functions as a vibrating section 66. The actuator section 58 is formed on the upper surface of the vibrating section 66.

The substrate 50 is constructed by laminating a plurality of green sheets made of zirconia ceramics (first thin plate layer 50A, first spacer layer 50B, second thin plate layer 50C, second spacer layer 50D, and third thin plate layer 50E), followed by sintering into one unit.

That is, the substrate 50 is constructed by laminating the thin-walled first thin plate layer 50A which is formed with a window for constructing the sample-pouring port 52 and which constitutes a part of the vibrating section 66, the thick-walled first spacer layer 50B which is formed with a part of the introducing bore 60 and a plurality of windows for constructing the cavity 56 respectively, the thin-walled second thin plate layer 50C which is formed with a part of the introducing bore 60 and a plurality of windows for constructing a part of the second communication hole 64 and the first communication hole 62 respectively, the thick-walled second spacer layer 50D which is formed with a plurality of windows for constructing a part of the introducing bore 60 and a part of the second communication hole 64 respectively, and the thin-walled third thin plate layer 50E which is formed with a window for constructing the sample discharge port 54, followed by sintering into one unit.

The actuator section 58 is constructed to have the vibrating section 66 described above as well as a lower electrode 70 which is directly formed on the vibrating section 66, a piezoelectric layer 72 which is composed of, for example, a piezoelectric/electrostrictive element or an anti-ferroelectric formed on the lower electrode 70, and an upper electrode 74 which is formed on the upper surface of the piezoelectric layer 72.

As shown in FIG. 4C, the lower electrode 70 and the upper electrode 74 are electrically connected to an unillustrated driving circuit via a plurality of pads 76, 78 which are formed on the upper surface of the substrate 50 respectively.

The micropipette 34 constructed as described above is operated as follows. That is, when an electric field is generated between the upper electrode 74 and the lower electrode 70, then the piezoelectric layer 72 is deformed, and the vibrating section 66 is deformed in accordance therewith. Accordingly, the volume of the cavity (pressurizing chamber) 56 contacting with the vibrating section 66 is decreased or increased.

When the volume of the cavity 56 is decreased, the sample solution charged in the cavity 56 is discharged at a predetermined speed from the sample discharge port 54 which communicates with the cavity 56. As shown in FIG. 3, it is possible to produce the DNA chip 20 in which the sample solutions discharged from the micropipettes 34 are aligned and fixed as spots 80 on the base plate 10 such as a microscopic slide glass. When the volume of the cavity 56 is increased, the sample solution is newly poured and charged from the first communication hole 62 into the cavity 56 to make provision for the next discharge.

An apparatus structure based on the so-called ink-jet system may be adopted as the structure in which the volume of the cavity 56 is decreased in accordance with the driving of the actuator section 58 (see Japanese Laid-Open Patent Publication No. 6-40030).

The cavity (pressurizing chamber) 56 is formed to have such a flow passage dimension that the sample solution containing DNA fragments or the like is moved without any turbulence.

Figure 6:
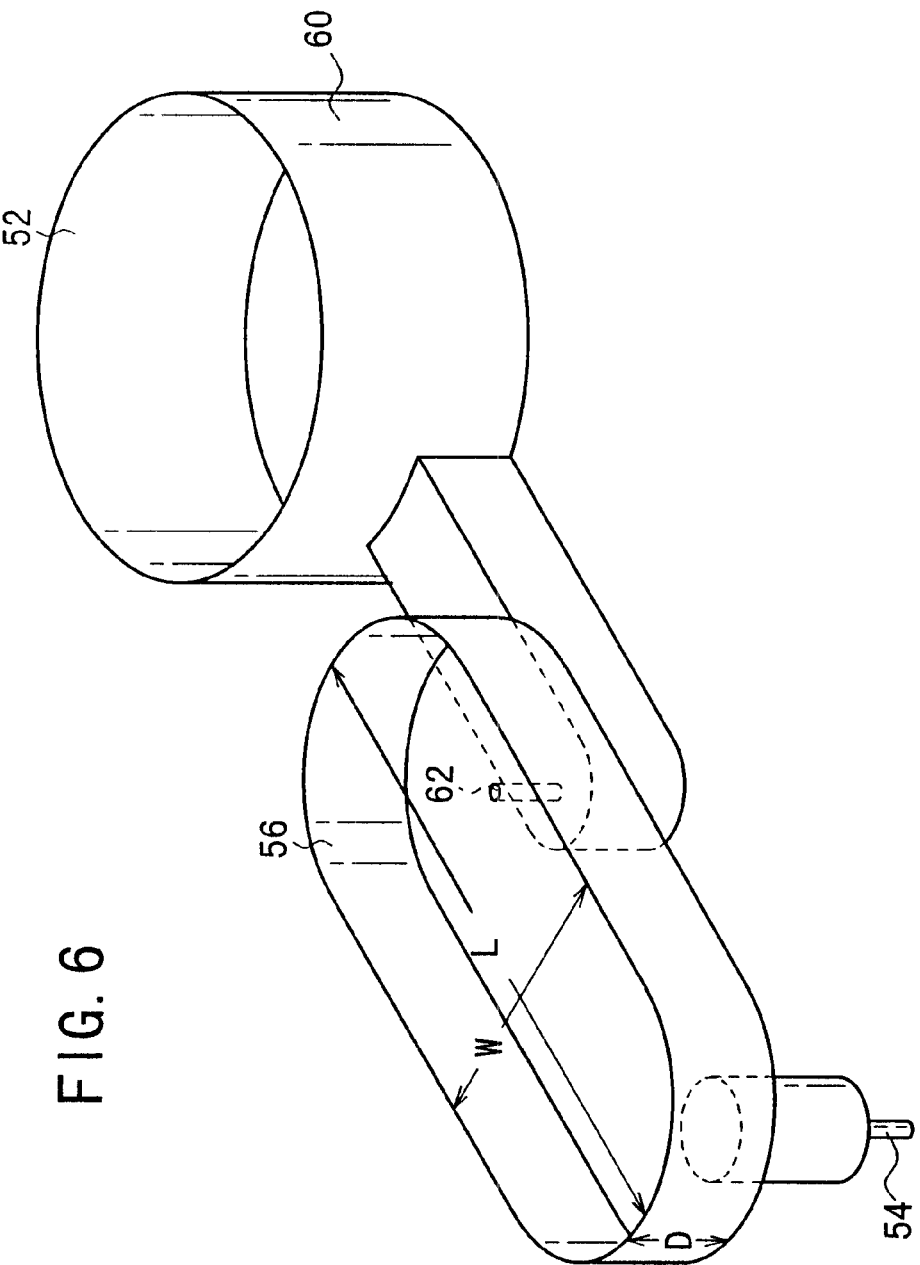
FIG. 6 shows a perspective view illustrating a shape of a flow passage including a cavity formed in a substrate of the micropipette.

That is, the dimension of the cavity 56 differs depending on the type of the sample, the size of liquid droplets to be prepared, and the density of spotting formation. However, for example, when DNA fragments which length is about 1 to 10,000 base pairs are dissolved in a×1 TE buffer solution at a concentration of not more than 100 $\mu g/\mu l$, and a sample, which is obtained by mixing with an aqueous solution containing an equivalent amount of polymer, is supplied at a pitch of 50 to 600 $\mu m$ to give a liquid droplet diameter of 30 to 500 $\mu m\phi$, then it is preferable that the cavity length (L) is 1 to 5 mm, the cavity width (W) is 0.1 to 1 mm, and the cavity depth (D) is 0.1 to 0.5 mm as shown in FIG. 6. It is preferable that the inner wall of the cavity 56 is smooth without involving any projection to disturb the flow. It is more preferable that the material of the cavity 56 is made of ceramics which has good affinity with respect to the sample solution.

When the shape as described above is adopted, the cavity 56 can be used as a part of the flow passage ranging from the sample-pouring port 52 to the sample discharge port 54. The sample solution can be introduced to the sample discharge port 54 without disturbing the flow of the sample solution which is moved from the sample-pouring port 52 via the introducing bore 60 and the first communication hole 62 to the inside of the cavity 56.

The substrate 50 is the sintered product obtained by laminating the zirconia ceramics into one unit as described above. Alternatively, the substrate 50 may be a bonded product composed of a sintered material of zirconia ceramics formed with the actuator section 58, and a metal or resin film or the like. Especially, the third thin plate layer 50E, in which the sample discharge port 54 is formed, is preferably a sheet obtained by processing an organic resin such as a PET film by means of an excimer laser or the like, or a sheet obtained by punching a metal such as a stainless steel film with a punch and die or the like, considering the matching with the processing method therefor.

The sizes of the sample discharge port 54 and the first communication hole 62 are optimally designed depending on, for example, the physical property, the discharge amount, and the discharge speed of the sample solution to be discharged. However, they are preferably about 10 to 100 $\mu m\phi$.

Figure 7:
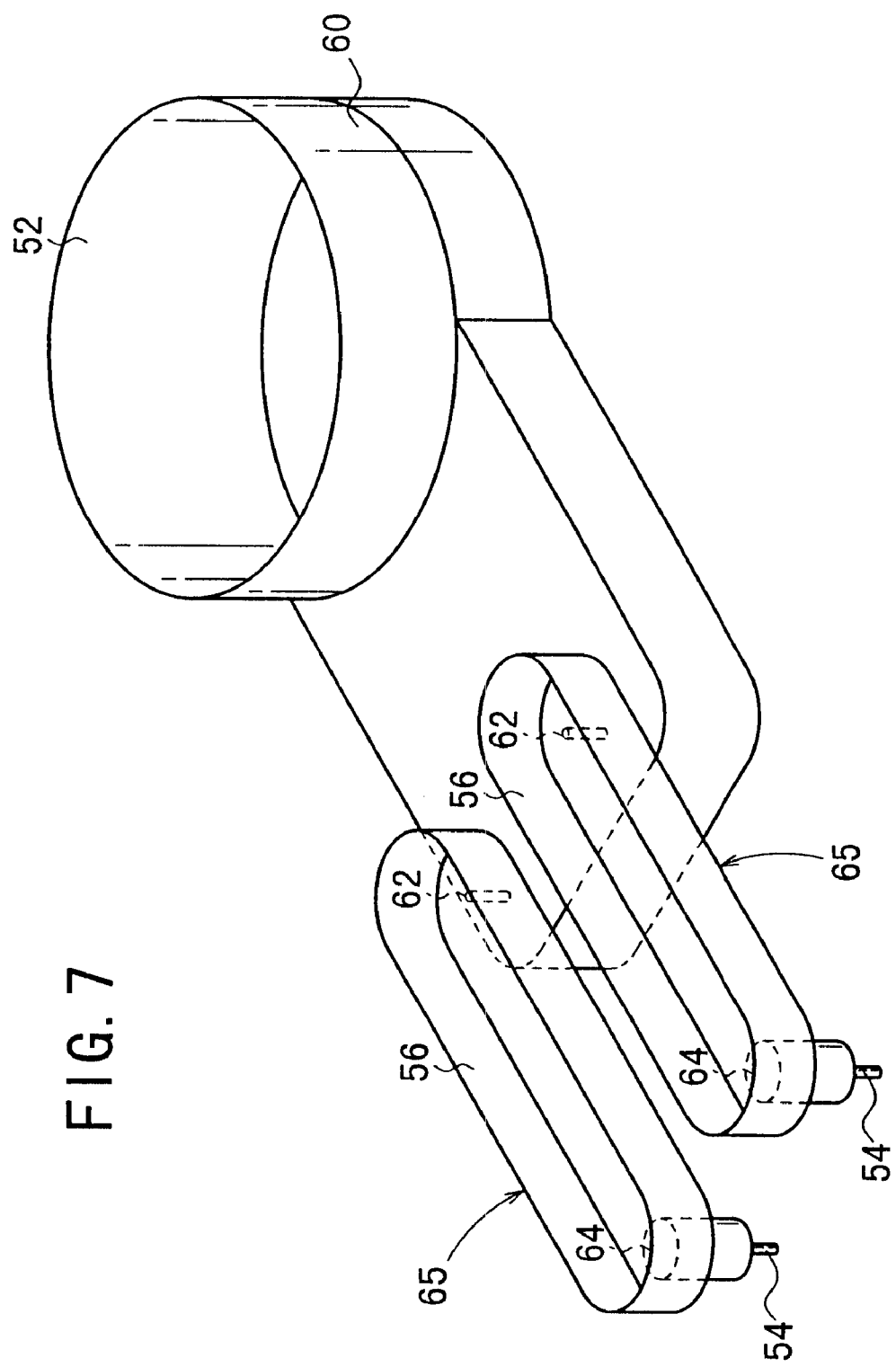
FIG. 7 shows a perspective view illustrating another shape of flow passages including cavities formed in a substrate of the micropipette.

In FIG. 7, two of the first communication holes 62 communicate with one sample-pouring port 52 and the introducing bore 60 connected thereto. Two flow passages 65, in each of which the cavity 56, the second communication hole 64, and the sample discharge port 54 are continuously formed, are independently formed for the respective communication holes 62 respectively. Actuator sections 58 (not shown), which are wired and driven independently respectively, are formed on the upper surfaces of the respective cavities 56. When the micropipette 34 constructed as described above is used, it is possible to supply an identical sample solution onto the base plate 10 simultaneously or at any deviated timing.

As shown in FIG. 4A, a plurality of pins 38 for positioning and fixing the micropipettes 34 are provided on the upper surface of the fixation plate 32. When the micropipette 34 is fixed on the fixation plate 32, the micropipette 34 is placed on the fixation plate 32 while inserting the pins 38 of the fixation plate 32 into positioning holes 90 (see FIG. 4C) provided at the both sides of the substrate 50 of the micropipette 34. Thus, a plurality of micropipettes 34 are automatically aligned and positioned with a predetermined array arrangement.

Each of the fixing jigs 36 has a holder plate 100 for pressing the plurality of micropipettes 34 against the fixation plate 32. Insertion holes for inserting screws 102 thereinto are formed through both end portions of the holder plate 100. When the screws 102 are inserted into the insertion holes, and they are screwed into the fixation plate 32, then the plurality of micropipettes 34 can be pressed against the fixation plate 32 by the aid of the holder plate 100 at once. One unit is constructed by the plurality of micropipettes 34 which are pressed by one holder plate 100. The example shown in FIG. 4A is illustrative of the case in which one unit is constructed by the five micropipettes 34 which are arranged in the direction of the column.

The holder plate 100 is formed with introducing holes 104 (see FIG. 4B) which are used to supply the sample solutions to the portions corresponding to the sample-pouring ports 52 of the respective micropipettes 34 respectively when the plurality of micropipettes 34 are pressed. Tubes 106 for introducing the sample solution to the introducing holes 104 respectively are held at upper end portions of the respective introducing holes 104.

Considering the realization of the efficient wiring operation, it is preferable that the width of the holder plate 100 resides in such a dimension that the pads 76, 78 connected to the respective electrodes 70, 74 of the actuator section 58 are faced upwardly when the plurality of micropipettes 34 are pressed against the fixation plate 32.

As described above, the dispenser 30 is constructed that the plurality of micropipettes 34 each having the sample-pouring port 52 and the sample discharge port 54 are provided in an upstanding manner with the respective sample discharge ports 54 directed downwardly.

That is, the respective micropipettes 34 are aligned and arranged such that the respective sample-pouring ports 52 are disposed on the upper side, the sample discharge ports 54 are disposed on the lower side, and the respective sample discharge ports 54 are aligned two-dimensionally. Sample solutions of mutually different types are discharged from the sample discharge ports 54 respectively.

Figure 8:
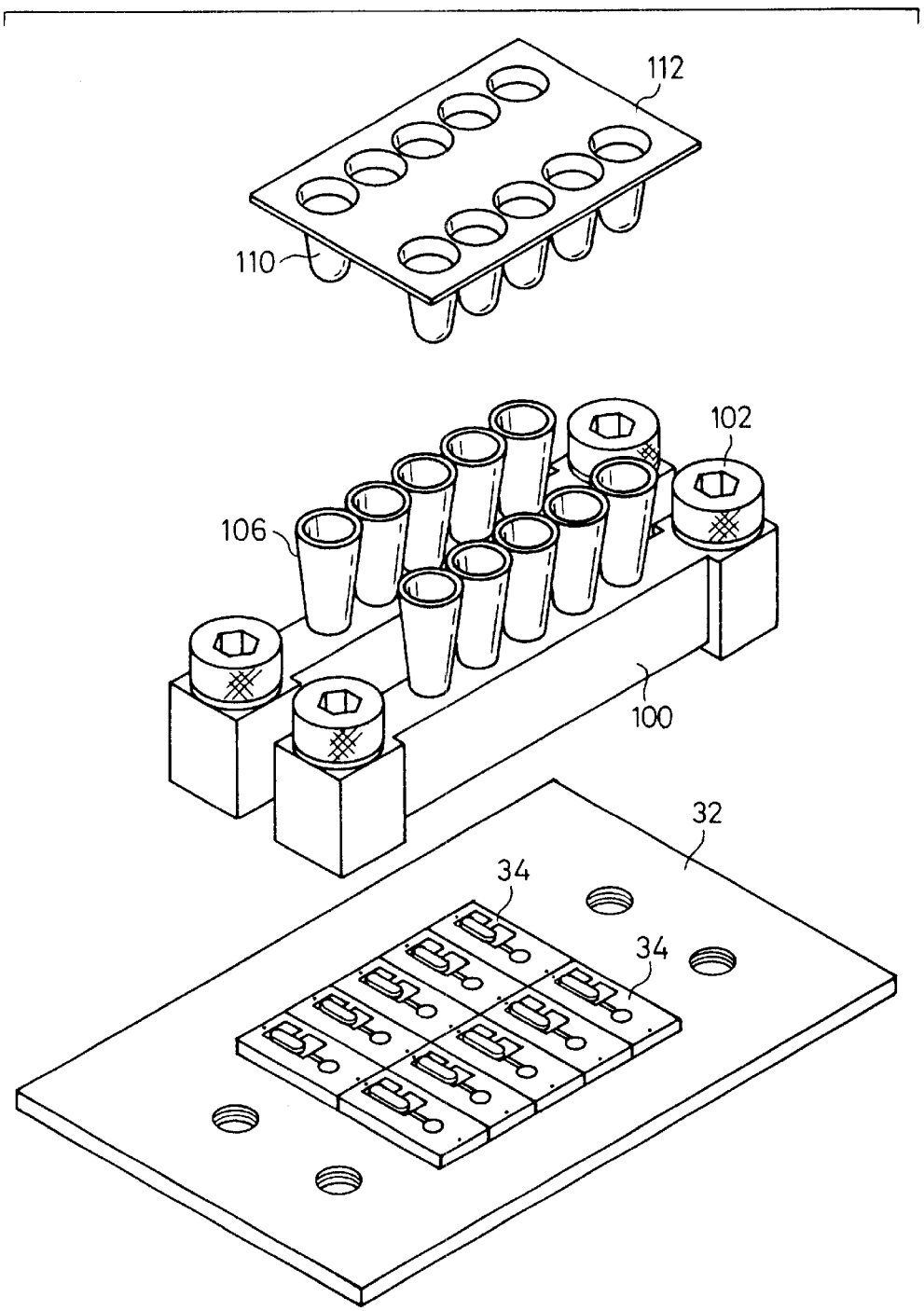
FIG. 8 shows an exploded perspective view illustrating the dispenser together with a cartridge.

When the dispenser 30 constructed as described above is used, several methods are available to supply the sample solutions of mutually different types corresponding to the respective sample-pouring ports 52. That is, as shown in FIG. 8, for example, a method is available, which is based on the used of a cartridge 112 arranged with a large number of recesses (storage sections) 110 each having a substantially V-shaped cross section. For this method, for example, the following procedure is available. That is, the mutually different sample solutions are poured into the respective recesses 110 of the cartridge 112. The cartridge 112 is attached so that the respective recesses 110 correspond to the tubes 106 respectively. The bottoms of the respective recesses 110 are opened with needles or the like. Accordingly, the sample solutions having been charged in the respective recesses 110 are supplied via the tubes 106 to the respective micropipettes 34.

When the tubes 106 are not used, for example, the following method is available. That is, the cartridge 112 is attached so that the respective recesses 110 correspond to the respective introducing holes 104 of the fixing jig 36. The bottoms of the respective recesses 110 are opened with needles or the like. Accordingly, the sample solutions having been charged in the respective recesses 110 are supplied via the introducing holes 104 to the respective micropipettes 34. Alternatively, needles or the like may be formed in the vicinity of the respective introducing holes 104 of the fixing jig 36 so that the respective recesses 110 may be opened simultaneously with the attachment of the cartridge 112 to the fixing jig 36.

Alternatively, it is also preferable to add a mechanism for feeding the gas or the like under the pressure after the opening to forcibly extrude the sample solutions. It is desirable to provide a mechanism for washing the space ranging from the sample-pouring port 52 to the sample discharge port 54 formed at the inside of the substrate 50 of each of the micropipettes 34, for example, in order that several thousands to several tens thousands types or many kinds of DNA fragments are discharged as the spots 80 with good purity without involving any contamination.

In the example shown in FIG. 4A, the both ends of the holder plate 100 are tightened to the fixation plate 32 by the aid of the screws 102. However, the holder plate 100 may be fixed in accordance with other methods based on the mechanical procedure by using screws and springs, as well as based on an adhesive or the like.

As described above, the substrate 50 for constructing the micropipette 34 is formed of ceramics, for which it is possible to use, for example, fully stabilized zirconia, partially stabilized zirconia, alumina, magnesia, and silicon nitride.

Among them, the fully stabilized/partially stabilized zirconia is used most preferably, because the mechanical strength is large even in the case of the thin plate, the toughness is high, and the reactivity with the piezoelectric layer 72 and the electrode material is small.

When the fully stabilized/partially stabilized zirconia is used as the material, for example, for the substrate 50, it is preferable that the portion (vibrating section 66), on which the actuator section 58 is formed, contains an additive such as alumina and titania.

Those usable as the piezoelectric ceramic for the piezoelectric layer 72 for constructing the actuator section 58 include, for example, lead zirconate, lead titanate, lead magnesium niobate, lead magnesium tantalate, lead nickel niobate, lead zinc niobate, lead manganese niobate, lead antimony stannate, lead manganese tungstate, lead cobalt niobate, and barium titanate, as well as composite ceramics containing components obtained by combining any of them. However, in the embodiment of the present invention, a material containing a major component composed of lead zirconate, lead titanate, and lead magnesium niobate is preferably used, because of the following reason.

That is, such a material has a high electromechanical coupling constant and a high piezoelectric constant. Additionally, such a material has small reactivity with the substrate material during the sintering of the piezoelectric layer 72, making it possible to stably form the product having a predetermined composition.

Further, in the embodiment of the present invention, it is also preferable to use ceramics obtained by appropriately adding, to the piezoelectric ceramics described above, for example, oxides of lanthanum, calcium, strontium, molybdenum, tungsten, barium, niobium, zinc, nickel, manganese, cerium, cadmium, chromium, cobalt, antimony, iron, yttrium, tantalum, lithium, bismuth, and stannum, or a combination of any of them, or other compounds.

For example, it is also preferable to use ceramics containing a major component composed of lead zirconate, lead titanate, and lead magnesium niobate, and further containing lanthanum and/or strontium.

On the other hand, it is preferable that the upper electrode 74 and the lower electrode 70 of the actuator section 58 are made of metal which is solid at room temperature and which is conductive. For example, it is possible to use metal simple substance of, for example, aluminum, titanium, chromium, iron, cobalt, nickel, copper, zinc, niobium, molybdenum, ruthenium, palladium, rhodium, silver, stannum, tantalum, tungsten, iridium, platinum, gold, and lead, or alloy obtained by combining any of them. It is also preferable to use a cermet material obtained by dispersing, in the metal described above, the same material as that of the piezoelectric layer 72 or the substrate 50.

Next, in this embodiment, the DNA chip 20 is produced by using the dispenser 30 as described above such that the spotted base plate, in which the sample solutions have been supplied onto the base plate 10, is left for about 1 hour in a thermostatic chamber at 80° C. to dry the spots 80 (drying step S5), followed by performing UV irradiation at 120 mJ, immersion in an NaBr solution for 20 minutes (blocking treatment), boiling for 2 minutes, and ethanol substitution (dehydration) to immobilize the DNA fragments on the base plate 10 (immobilization step S6).

Next, explanation will be made with reference to FIGS. 9 to 15 for several methods for supplying the sample solutions onto the base plate 10 to form the spots 80 by using the dispenser 30.

Figure 9:
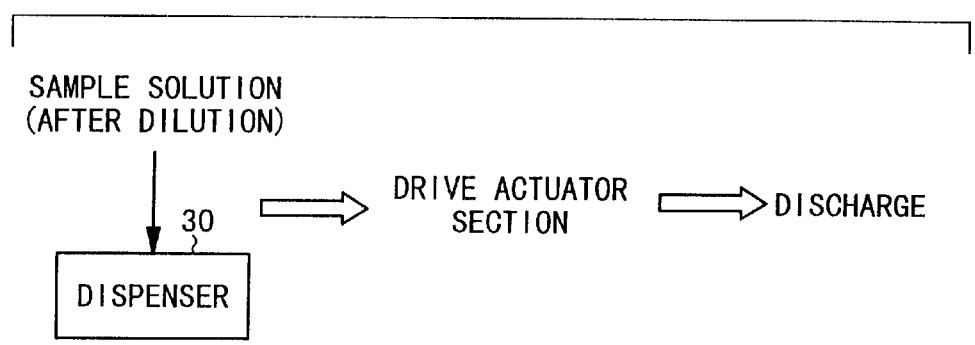
FIG. 9 illustrates a first method adopted when the DNA chip is produced by using the dispenser.

At first, a first method is shown in FIG. 9. In this method, the mutually different types of the sample solutions (after the dilution) are charged from the respective tubes 106 via the introducing holes 104 of the fixing jig 36 respectively into the cavities 56 of the respective micropipettes 34. Subsequently, the respective actuator sections 58 are driven to discharge the sample solutions from the sample discharge ports 54 of the respective micropipettes 34.

As for the electrical signal to be applied to each of the electrodes 70, 74 of the actuator section 58, when the actuator section 58 performs the ON operation to decrease the volume of the cavity 58, the pulse-shaped voltage is applied to each of the electrodes 70, 74. In this procedure, for example, the displacement amount and the displacement speed of the vibrating section 66 are changed by changing, for example, the amplitude (voltage) of the pulse, the amount of change per unit time (rising angle of the voltage waveform), and the pulse width. Accordingly, it is possible to control the discharge amount of the sample solution. The number of dripping operations for the sample solution per unit time can be altered by changing the number of pulses to be generated during a certain period.

Figure 10A:
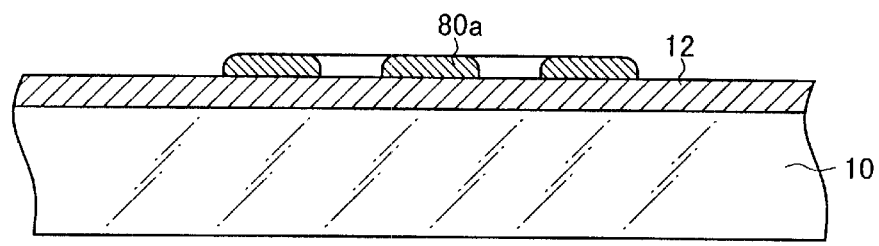
FIG. 10A shows a sectional view illustrating the process in which a sample solution is supplied onto a base plate, and a large number of minute spots are progressively formed in one spot to be formed.
Figure 10B:
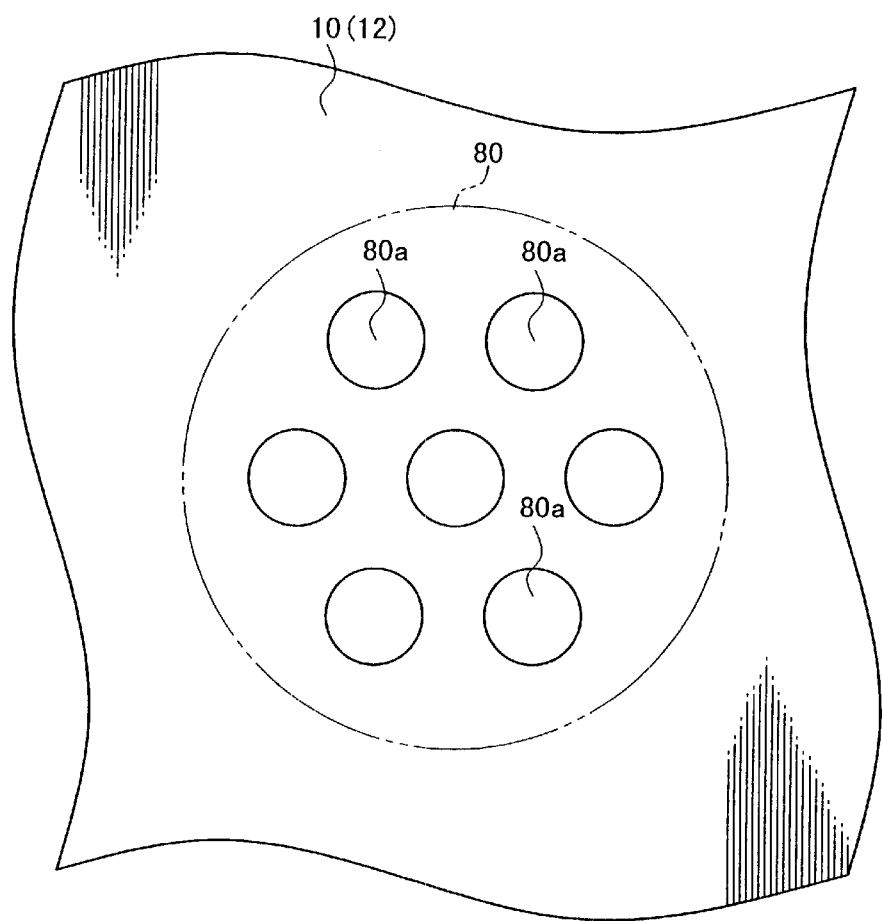
FIG. 10B shows a plan view thereof.
Figure 11A:
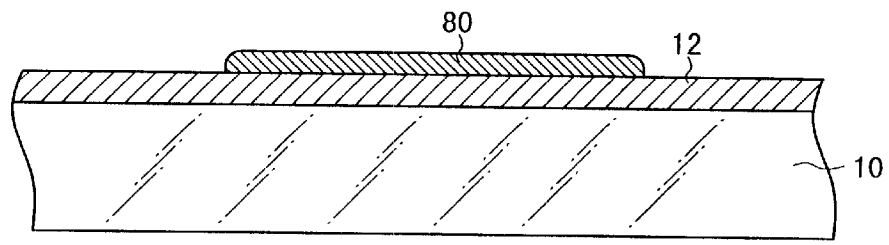
FIG. 11A shows a sectional view illustrating a state in which a large number of minute spots are combined to form one spot on the base plate.
Figure 11B:
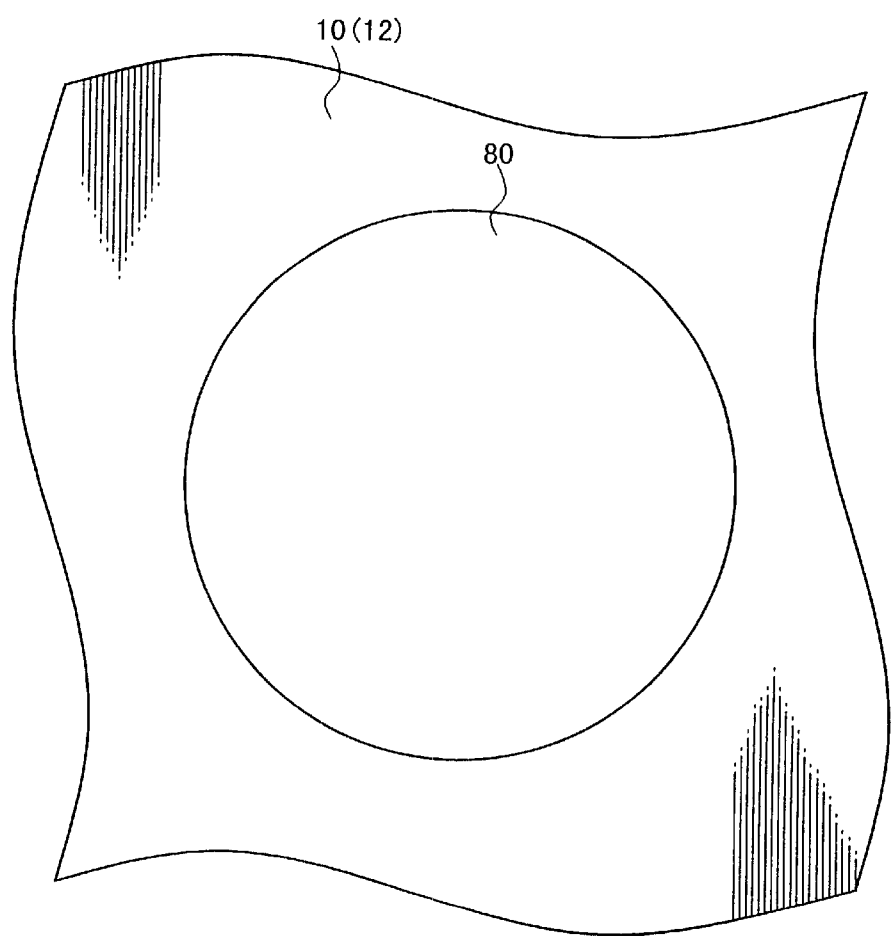
FIG. 11B shows a plan view thereof.

When one spot 80 is formed by supplying a plurality of drops of the sample solution, the number of supply times is usually increased while fixing the supply position. However, the supply position may be deviated every time the supply is performed. For example, as shown in FIGS. 10A and 10B, minute spots 80a based on a plurality of drops of the sample solution are formed within one spot 80 (indicated by a two-dot chain line) to be formed, by appropriately changing the supply position of the sample solution. The minute spots 80a are combined (integrated) on the base plate 10. Accordingly, as shown in FIGS. 11A and 11B, one spot 80 is formed. In this process, it is possible to obtain a uniform diameter of the respective spots 80 formed on the base plate 10, by controlling the number of supply times, the supply position, and the supply amount for one time of operation, depending on the type of the sample solution to be supplied.

Figure 12A:
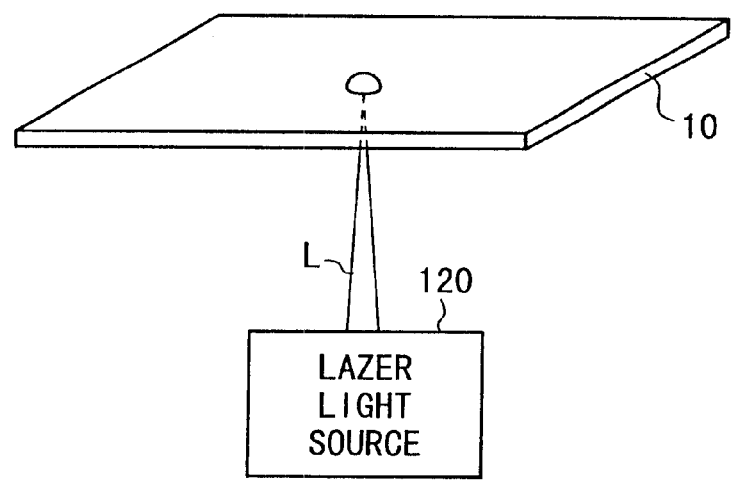
FIG. 12A illustrates an example of a method for heating the sample solution or the base plate.
Figure 12B:
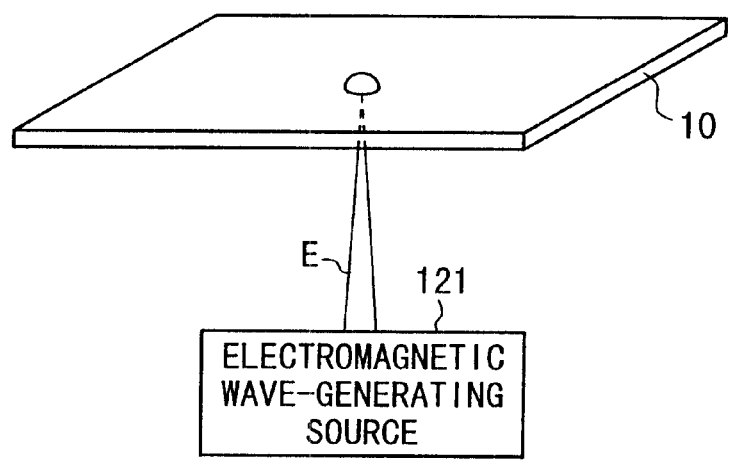
FIG. 12B illustrates another method for heating the sample solution or the base plate.
Figure 13:
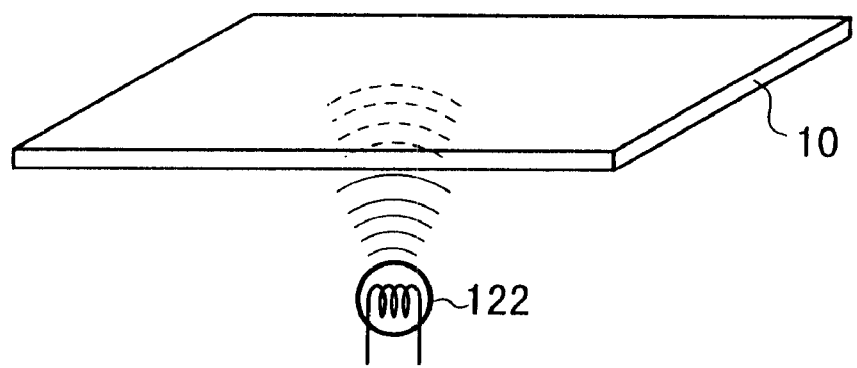
FIG. 13 illustrates an example of a method for heating the base plate.

Further, in this embodiment, when the sample solution is supplied onto the base plate 10, as shown in FIGS. 12A to 13, the portion of the sample solution is dried, thickened, or solidified. This treatment can be realized, for example, by heating the base plate 10.

As shown in FIG. 13, the method for heating the base plate 10 includes a method in which the back surface of the base plate 10 is irradiated with an infrared ray radiated from an infrared ray lamp 122. As shown in FIGS. 12A and 12B, the method for directly heating the sample solution includes a method in which a laser beam L or an electromagnetic wave E, which is radiated from a laser light source 120 or an electromagnetic wave-generating source 121, is focused on the sample solution to effect radiation and heating. The sample solution may be heated in a state of being supplied onto the base plate 10. However, in view of the stability of the shape upon the supply and the prevention of any expansion of the spot 80, it is desirable that the sample solution is radiated and heated during a period in which the sample solution is discharged from the sample discharge port 54, and it falls onto the base plate 10.

The electromagnetic wave E makes it possible to selectively heat those containing water such as the sample solution. Therefore, it is possible to heat only the sample solution (sample solution during the supply) for forming the spot 80, and hence the electromagnetic wave E is more preferred. When the heating is performed, the sample discharge port 54 completed for the discharge may be shielded with a metal shield or the like, in order to avoid any defective discharge which would be otherwise caused by being dried.

Further, in this embodiment, when the sample solution is supplied onto the base plate 10, the sample solution and the base plate 10 are cooled. The following cooling methods are available. That is, the base plate 10, to which the sample solution is supplied, may be previously cooled to be not more than room temperature. Alternatively, a cooling agent, which is composed of, for example, alternative from gas or liquid nitrogen, may be sprayed onto the sample solution itself. However, in the cooling treatment as described above, it is feared that water droplets adhere due to dew formation of water from surrounding gas during the cooling, and the spot 80 itself flows away. Therefore, for example, it is necessary to manage the humidity of the surrounding gas and manage the speed of the cooling and the restoration to ordinary temperature.

It is preferable to apply a voltage of such a degree as to excite the vibration in the actuator section 58 after charging the sample solution into the cavity 56. Accordingly, the DNA fragment, which is contained in the sample solution charged in the cavity, is uniformly dispersed. No dispersion arises in the amount of the DNA fragment for each time of the dripping.

Figure 14:
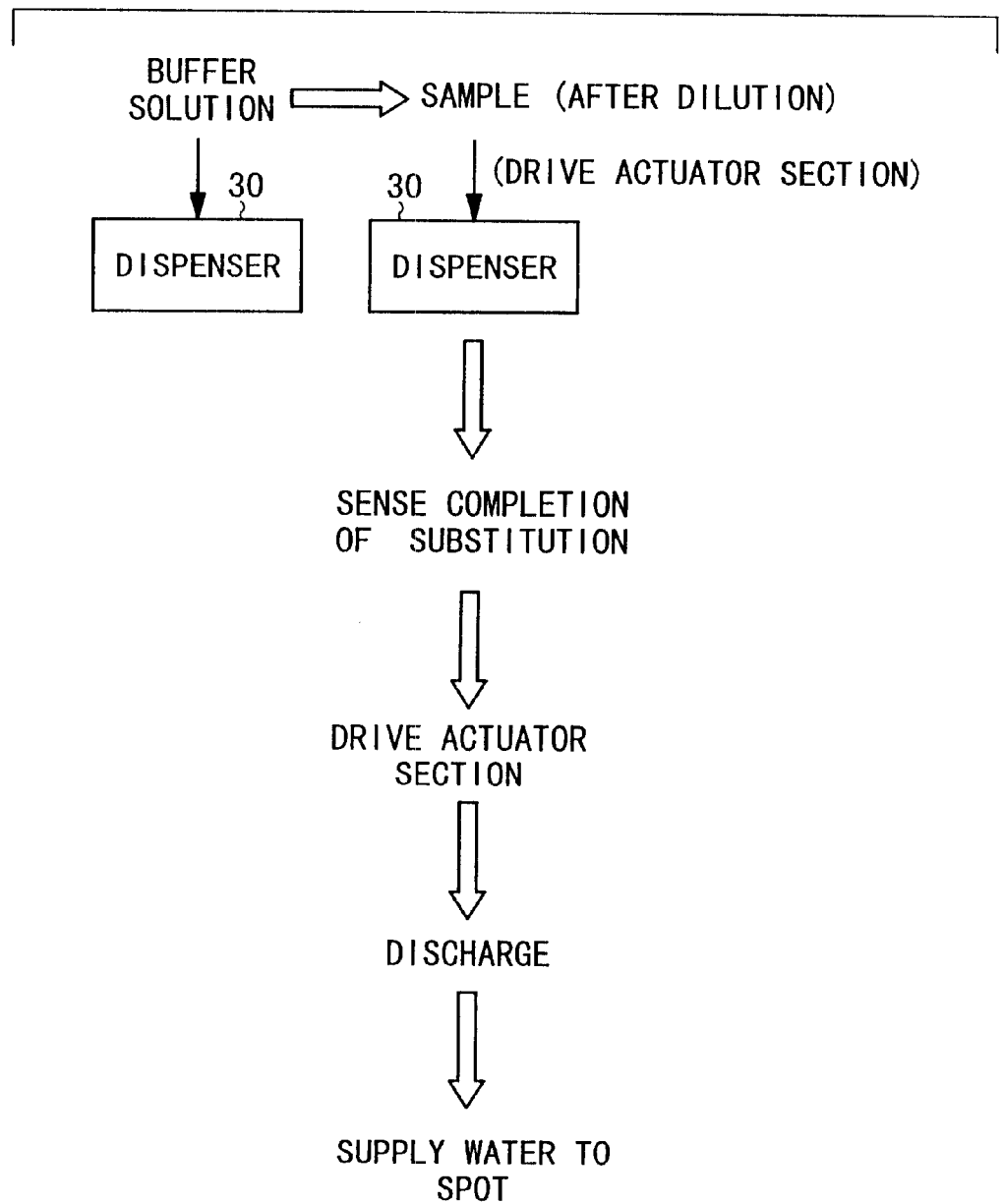
FIG. 14 illustrates a second method adopted when the DNA chip is produced by using the dispenser.

Next, explanation will be made for a second method based on the use of the dispenser 30. In the second method, as shown in FIG. 14, a substitution solution such as purified water or a buffer solution is charged into the cavities 56 of the respective micropipettes 34 from the respective tubes 106 via the introducing holes 104 of the fixing jig 36 respectively. Subsequently, the previously diluted samples are poured from the sample-pouring ports 52 into the cavities 56 while effecting substitution. The sample solutions are discharged and supplied onto the base plate 10 by driving the actuator sections 58. An intermediate solution (for example, a mixed solution of a buffer solution and an aqueous solution containing a polymer) containing no DNA fragment, which has approximately the same specific gravity as that of the sample solution, may be allowed to intervene between the substitution solution and the sample solution.

It is preferable that the completion of the laminar flow substitution of the sample in the cavity 56 is recognized by sensing the change of the fluid characteristic in the cavity 56.

It is preferable that the substitution between the substitution solution and the sample in the cavity 56 is performed in a form of the laminar flow. However, when the type of the sample is changed, or when the movement speed of the liquid is extremely fast, it is not necessarily indispensable to effect the laminar flow at portions of the cavity 56 in the vicinity of the first communication hole 62. In this case, the purge amount of the sample solution is increased due to the mixing of the sample solution and the substitution solution. However, it is possible to suppress the increase in the purge amount to be minimum by judging the completion of the substitution by sensing the change of the fluid characteristic in the cavity 56.

In the present invention, the change of the fluid characteristic in the cavity 56 is recognized by applying a voltage in such a degree as to excite the vibration in the actuator section 58, and detecting the change of the electric constant caused by the vibration. Such a procedure for sensing the change of the fluid characteristic is disclosed, for example, in Japanese Laid-Open Patent Publication No. 8-201265. Reference may be made to the contents of this patent document.

Specifically, the electric connection from a power source for driving the discharge is separated from the actuator section 58 at a predetermined interval by using a relay. Simultaneously, a means for measuring the resonance frequency is connected by using the relay. At this point of time, the impedance or the resonance frequency is electrically measured.

Accordingly, it is possible to recognize, for example, whether or not the viscosity and the specific gravity of the liquid are those of the objective sample (liquid containing the DNA fragment or the like). That is, as for each of the micropipettes 34, the micropipette 34 itself functions as a sensor. Therefore, it is also possible to simplify the structure of the micropipette 34.

After the substitution, the actuator section 58 is driven under a driving condition corresponding to the amount of liquid droplets suitable for the required spot diameter, and the sample solution is repeatedly supplied onto the base plate 10. Accordingly, the DNA chip 20 is produced. Usually, when one spot 80 is formed, one to several hundreds of droplet or droplets are discharged from the micropipette 34.

When the amount of the sample in the sample-pouring port 52 is decreased, the discharge is continued by adding the buffer solution, the purified water, or the aqueous solution containing sodium chloride so that no bubble enters the inside of the flow passage. Accordingly, all of the sample solution can be used without allowing the sample solution to remain in the micropipette 34. The completion of the substitution from the sample to the substitution solution (completion of the sample discharge) is confirmed by detecting the viscosity and the specific gravity of the liquid by using the actuator section 58 in the same manner as described above.

It is preferable to use the substitution solution, the intermediate solution, and the sample solution such that the dissolved gas in the solution is previously removed by performing the degassing operation. When such a solution is used, if any bubble obstructs the flow passage at an intermediate portion to cause the defective charge upon the charge of the solution into the flow passage of the micropipette 34, then the inconvenience can be avoided by dissolving the bubble in the sample solution. Further, no bubble is generated in the fluid during the discharge, and no defective discharge is caused as well.

In the second method described above, the substitution solution such as the buffer solution, the purified water, and the aqueous solution containing sodium chloride is poured from the sample-pouring port 52 into the cavity while discharging the sample solution, and the sample solution remaining in the cavity 56 is completely discharged in accordance with the laminar flow substitution in the same manner as described above to make provision for the next pouring of the sample.

When it is sensed whether or not the sample solution remains in the cavity 56 (whether or not the discharge can be effected as the sample solution), the recognition can be also made by sensing the change of the fluid characteristic in the cavity 56. In this case, a mechanism for detecting the completion of the laminar flow substitution or the substitution can be used to extremely decrease the purge amount of the sample which is not used and improve the efficiency of the use of the sample solution.

It is also preferable that when the sample is charged from the sample-pouring port 52 to the cavity 56, the interior of the cavity 56 is subjected to the laminar flow substitution with the sample from the sample-pouring port 52 while driving the actuator section 58. In this procedure, the interior of the cavity 56 can be completely substituted in a reliable manner with the inexpensive substitution solution beforehand, and then the laminar flow substitution is effected with the expensive sample. As a result, it is possible to completely avoid the occurrence of any defective discharge, and it is possible to efficiently discharge the expensive sample.

Figure 15:
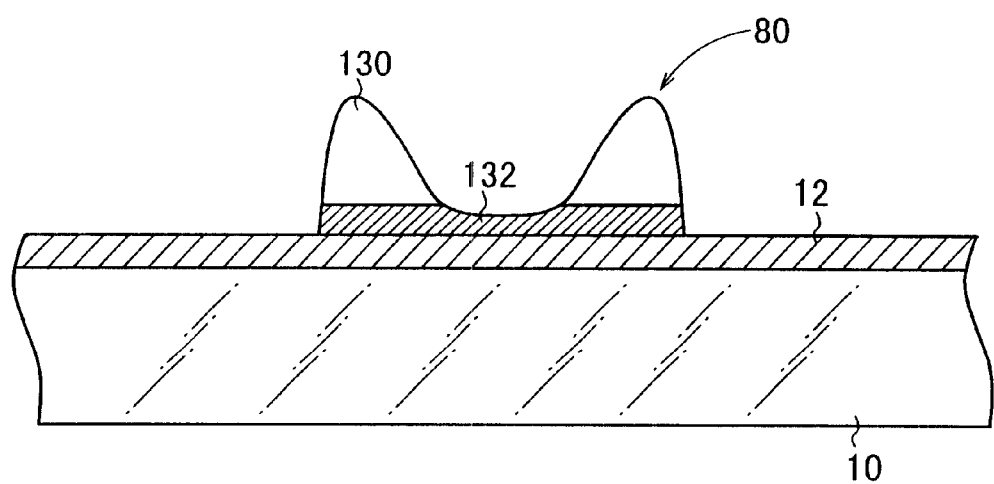
FIG. 15 shows a sectional view illustrating an example of a spot having a doughnut-shaped configuration.
Figure 16:
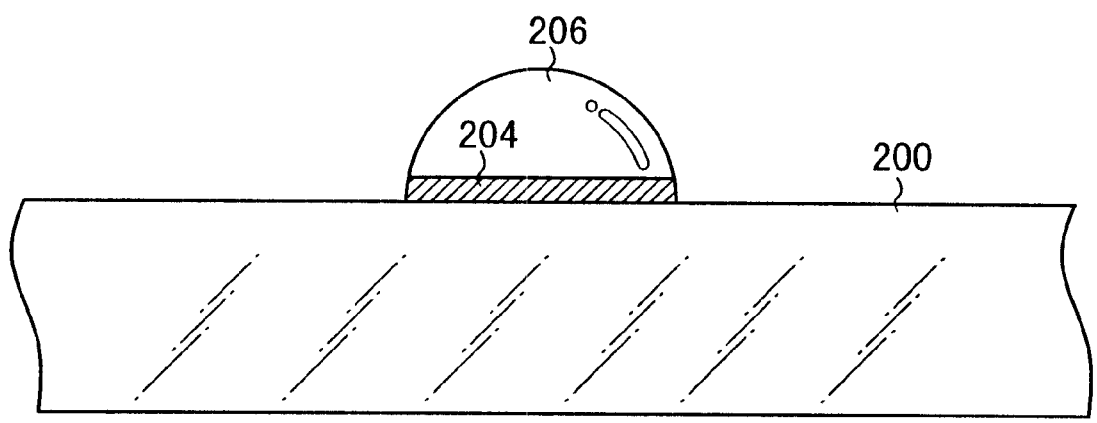
FIG. 16 shows a sectional view illustrating a shape of a spot formed on a base plate in accordance with a method for producing a DNA chip concerning the illustrative conventional technique.

Subsequently, when the thickness shape of the spot 80 on the base plate 10 supplied with the sample solution is a so-called doughnut-shaped configuration with the bulge at its circumferential edge portion 130 as shown in FIG. 15, then the base plate 10 is cooled to 0° C. followed by performing a treatment to make restoration to an atmosphere at room temperature in which a sufficient volume of gas exists at a humidity of not less than 30%. By doing so, water is supplied to the spot 80 having the doughnut-shaped configuration. The fluidity of the sample solution in the spot 80 is increased, and the spot 80 is changed to have a hemispherical configuration in accordance with the surface tension. Thus, the bulge at the circumferential edge portion 130 disappears.

In the case of the doughnut-shaped configuration, the boundary between the base plate 10 and the circumferential edge portion 130 of the spot 80 is conspicuous, and it is easily observed. When the spot 80 of the colorless and transparent liquid such as the sample solution containing the DNA fragment is formed, for example, on the colorless and transparent glass base plate, the following advantage is obtained. That is, it is easy to observe the shape of the spot, and it is easy to inspect whether the shape of the spot is satisfactory or defective.

However, in the case of the spot 80 having the doughnut-shaped configuration as described above, the substantial immobilized sample 132 is plentiful (thick) at the circumferential edge portion 130, even when most of the circumferential edge portion 130 (bulged portion) is washed away in the washing step during the immobilization to be performed thereafter. Therefore, in the case of the use as the DNA chip 20, the distribution of fluorescence emission amount emitted from the spot 80 exhibits a doughnut-shaped configuration in the spot 80, consequently causing a factor to bring about the dispersion and the deterioration of the sensitivity.

Therefore, in order to realize both of the easy inspection (doughnut-shaped configuration) and the good shape of the spot (non-doughnut-shaped configuration), the following method is appropriate. That is, when the sample solution is supplied onto the base plate 10, the discharge is performed in accordance with the ink-jet system or the like to supply the sample solution onto the base plate 10 so that the sample solution is concentrated at the circumferential edge portion 130 of the spot 80 by controlling the kinetic energy and the hydrophobic property with respect to the base plate 10 to form the doughnut-shaped configuration.

After that, the viscosity of the sample solution is previously increased to such an extent that the spot 80 is not spherical against the surface tension of the liquid, while the fluidity of the sample solution to form the spot 80 is increased after completion of the inspection so that the doughnut-shaped configuration is changed to the non-doughnut-shaped configuration by the aid of the surface tension.

The method described above can be easily realized in accordance with the method according to the embodiment of the present invention (treatment in which the base plate 10 is cooled to 0° C. and then the base plate 10 is returned in the atmosphere at room temperature in which the sufficient volume of gas exists at the humidity of not less than 30%).

In order to supply water to the spot 80, water vapor containing mist or the like may be directly applied. However, it is preferable to utilize the water formed by dew formation on the base plate 10 during the step of restoration to the room temperature after the cooling, in view of the fact that the spot does not flow away due to any excessive water, and fine water droplets are uniformly supplied.

After that, the spot 80 is dried by baking the base plate 10 at 80° C. for 1 hour. A step of cooling and restoration to room temperature may be applied after the baking at 80° C. for 1 hour. However, in this case, it is necessary to perform the baking treatment again.

As described above, in the method for producing the DNA chip according to the embodiment of the present invention, the concentration of the sample solution is diluted before the sample solution is supplied onto the base plate 10. Therefore, when the sample solution is supplied onto the base plate 10, the spot 80 of the sample solution is not ehemispherical, but it has the flat shape as shown in FIG. 11A. In this case, almost all of the supplied sample solution is immobilized. Accordingly, most of, or more of the sample solution is not washed away even in the washing step performed thereafter. Thus, it is possible to improve the efficiency of the use of the sample solution.

The viscosity and the surface tension of the sample solution are changed by varying the degree of the dilution depending on the type of the DNA fragment contained in the sample solution. Accordingly, it is possible to realize the uniform diameter of the spot 80 formed on the base plate 10.

The step of supplying water to the spot 80 is added after the sample solution is supplied onto the base plate 10 to form the spot 80. Accordingly, it is possible to obtain the further uniform shape of the spot 80 in the thickness direction.

As described above, in the embodiment of the present invention, it is possible to improve the efficiency of the use of the expensive sample solution. It is possible to improve the productivity of the DNA chip 20 and improve the yield. Further, it is possible to control the supply depending on the type of the sample solution to be supplied, it is possible to realize the uniform spot diameter formed on the base plate 10, and it is possible to improve the reliability and the quality of the DNA chip 20.

It is a matter of course that the method for producing the DNA chip according to the present invention is not limited to the embodiments described above, which may be embodied in other various forms without deviating from the gist or essential characteristics of the present invention.

As explained above, according to the method for producing the DNA chip concerning the present invention, it is possible to improve the efficiency of the use of the expensive sample solution, and it is possible to improve the productivity of the DNA chip and improve the yield. Further, it is possible to control the dripping depending on the type of the sample solution to be dripped, it is possible to realize the uniform spot diameter formed on the base plate, and it is possible to improve the reliability and the quality of the DNA chip.

What is claimed is:

1. A method for producing a DNA chip including a large number of spots of sample solutions arranged on a base plate, said method comprising the steps of:

providing a dispenser comprising a plurality of arranged micropipettes each including a pouring port for pouring said sample solution from the outside, a cavity for pouring and charging said sample solution thereinto, and a discharge port for discharging said sample solution, formed on at least one substrate, so that said sample solution is movable in said cavity; and supplying sample solution of an identical type from at least two of said discharge ports of said dispenser onto the base plate a plurality of times to form one of said spots, wherein said sample solution is subjected to at least one of drying, thickening and solidifying treatments while said sample solution is being supplied.

2. The method for producing said DNA chip according to claim 1, wherein one pouring port communicates with said cavity connected with at least two or more of said discharge ports for discharging said sample solution of said identical type.

3. The method for producing said DNA chip according to claim 1, wherein said sample solution of said identical type is discharged substantially simultaneously from at least two or more of said discharge ports.

4. The method for producing said DNA chip according to claim 1, wherein said sample solution of said identical type is discharged at deviated discharge timings from at least two or more of said discharge ports respectively.

5. A method for producing a DNA chip including a large number of spots of sample solutions arranged on a base plate, said method comprising tie steps of:

providing a dispenser comprising a plurality of arranged micropipettes each including a pouring port for pouring said sample solution from the outside, a cavity for pouring and charging said sample solution thereinto, and a discharge port for discharging said sample solution, formed on at least one substrate, said micropipettes comprising piezoelectric/electrostrictive elements disposed on at least one wall surface of said at least one substrate which forms said cavities so that said sample solution is movable in said cavities;

charging a substitution solution into said cavities;

pouring different types of said sample solution into said pouring ports to effect substitution within each respective cavity; and driving said piezoelectric/electrostrictive elements so tat mutually different types of said sample solution in said cavities are discharged from said discharge ports, wherein said sample solution is supplied onto the base plate a plurality of times to form one of said spots, said sample solution being subjected to at least one of drying, thickening and solidifying treatments while said sample solution is being supplied.

6. The method for producing said DNA chip according to claim 5, wherein said substitution solution is previously charged into said plurality of cavities, and said different types of said sample solutions are poured from said pouring ports while effecting said substitution in said plurality of cavities, while driving said piezoelectric/electrostrictive elements.

7. The method for producing said DNA chip according to claim 5, wherein completion of pouring or substitution of said sample solutions in said plurality of cavities is recognized by sensing a change of a fluid characteristic in said cavity.

8. The method for producing said DNA chip according to claim 5, wherein said substitution solution is previously subjected to a degassing treatment.

9. The method for producing said DNA chip according to claim 5, wherein said substitution solution is previously charged into said plurality of cavities, an intermediate solution containing no DNA fragment, which has approximately the same specific gravity as that of said sample solution, is subsequently poured from said pouring ports while effecting substitution in said cavities, said different types of said sample solutions are subsequently poured from said pouring ports into said cavities, and said piezoelectric/electrostrictive elements are driven so that said different types of said sample solutions in said plurality of cavities are discharged from said discharge ports.

10. A method for producing a DNA chip including a large number of spots of sample solutions arranged on a base plate, said method comprising the steps of:

supplying said sample solution onto the base plate a plurality of times to form one of said spots; and subjecting said sample solution to at least one of drying, thickening and solidifying treatments while said sample solution is being supplied, wherein said treatment of drying, thickening, or solidifying said sample solution comprises a treatment of heating said base plate.

11. A method for producing a DNA chip including a large number of spots of sample solutions arranged on a base plate, said method comprising the steps of:

supplying said sample solution onto the base plate a plurality of times to form one of said spots; and subjecting said sample solution to at least one of drying, thickening and solidifying treatments while said sample solution is being supplied, wherein said treatment of drying, thickening, or solidifying said sample solution comprises heating said discharged or supplied sample solution.

12. A method for producing a DNA chip including a large number of spots of sample solutions arranged on a base plate, said method comprising the steps of:

supplying said sample solution onto the base plate a plurality of times to form one of said spots; and subjecting said sample solution to at least one of drying, thickening and solidifying treatments while said sample solution is being supplied, wherein a laser beam is used for said treatment of drying, thickening, or solidifying said sample solution.

13. A method for producing a DNA chip including a large number of spots of sample solutions arranged on a base plate, said method comprising the steps of:

supplying said sample solution onto the base plate a plurality of times to form one of said spots; and subjecting said sample solution to at least one of drying, thickening and solidifying treatments while said sample solution is being supplied, wherein an infrared ray is used for said treatment of drying, thickening, or solidifying said sample solution.

14. A method for producing a DNA chip including a large number of spots of sample solutions arranged on a base plate, said method comprising the steps of:

supplying said sample solution onto the base plate a plurality of times to form one of said spots; and subjecting said sample solution to at least one of drying, thickening and solidifying treatments while said sample solution is being supplied, wherein an electromagnetic wave is used for said treatment of drying, thickening, or solidifying said sample solution.

15. A method for producing a DNA chip including a large number of spots of sample solutions arranged on a base plate, said method comprising the steps of:

supplying said sample solution onto the base plate a plurality of times to form one of said spots; and subjecting said sample solution to at least one of drying, thickening and solidifying treatments while said sample solution is being supplied, wherein said treatment of drying, thickening, or solidifying said sample solution comprises a treatment of cooling said base plate or said discharged or supplied sample solution.

16. A method for producing a DNA chip including a large number of spots of sample solutions arranged on a base plate, said method comprising the steps of:

supplying said sample solution onto the base plate a plurality of times to form one of said spots;

subjecting said sample solution to at least one of drying, thickening and solidifying treatments while said sample solution is being supplied; and cooling said base plate to be not more than 0° C. after preparing said base plate on which said large number of spots are arranged, and then returning said base plate to room temperature in an atmosphere in which a sufficient volume of gas exists at a humidity of not less than 30%.

17. A method for producing a DNA chip including a large number of spots of sample solutions arranged on a base plate, said method comprising the steps of:

supplying said sample solution onto the base plate a plurality of times to form one of said spots;

subjecting said sample solution to at least one of drying, thickening and solidifying treatments while said sample solution is being supplied; and exposing said base plate in an atmosphere in which a sufficient volume of gas exists at a humidity of not less than 80% after preparing said base plate on which said large number of spots are arranged by supplying said sample solutions onto said base plate.

18. A method for producing a DNA chip including a large number of spots of sample solutions arranged on a base plate, said method comprising the steps of:

supplying said sample solution onto the base plate a plurality of times to form one of said spots;

subjecting said sample solution to at least one of drying, thickening and solidifying treatments while said sample solution is being supplied; and exposing said base plate in water vapor containing mist after preparing said base plate on which said large number of spots are arranged by supplying said sample solutions onto said base plate.

19. A method for producing a DNA chip including a large number of spots of sample solutions arranged on a base plate, said method comprising the step of supplying said sample solutions onto said base plate in accordance with an ink-jet system, wherein:

when said sample solution is supplied onto said base plate, a humidity around a portion to which said sample solution is discharged and supplied is selectively increased as compared with that around the other portions so that said sample solution is not dried, thickened, or solidified.

20. The method for producing said DNA chip according to claim 19, further comprising the steps of cooling said base plate to be not more than 0° C. after preparing said base plate on which said large number of spots are arranged by supplying said sample solutions onto said base plate, and then returning said base plate in an atmosphere at room temperature in which a sufficient volume of gas exists at a humidity of not less than 30%.

21. The method for producing said DNA chip according to claim 19, further comprising the step of exposing said base plate in an atmosphere in which a sufficient volume of gas exists at a humidity of not less than 80% after preparing said base plate on which said large number of spots are arranged by supplying said sample solutions onto said base plate.

22. The method for producing said DNA chip according to claim 19, further comprising the step of exposing said base plate in water vapor containing mist after preparing said base plate on which said large number of spots are arranged by supplying said sample solutions onto said base plate.

23. A method for producing a DNA chip including a large number of spots of at least one sample solution arranged on a base plate, said method comprising the steps of:

providing a dispenser comprising a plurality of arranged micropipettes each including a pouring port for pouring said sample solution from the outside, a cavity for pouring and charging said sample solution thereinto, and a discharge port for discharging said sample solution, formed on at least one substrate, so that said sample solution is movable in said cavity; and supplying at least one sample solution from at least two of said discharge ports of said dispenser onto the base plate a plurality of times to form one of said spots.

24. The method for producing said DNA chip according to claim 23, wherein one pouring port communicates with said cavity connected with at least two or more of said discharge ports for discharging said sample solution.

25. The method for producing said DNA chip according to claim 23, wherein said sample solution is discharged substantially simultaneously from said at least two of said discharge ports.

26. The method for producing said DNA chip according to claim 23, wherein said sample solution is discharged at deviated discharge timings from said at least two of said discharge ports.

27. A method for producing a DNA chip including a large number of spots of at least one sample solution arranged on a base plate, said method comprising the steps of:

providing a dispenser comprising a plurality of arranged micropipettes each including a pouring port for pouring said sample solution from the outside, a cavity for pouring and charging said sample solution thereinto, and a discharge port for discharging said sample solution, formed on at least one substrate, said micropipettes comprising piezoelectric/electrostrictive elements disposed on at least one wall surface of said at least one substrate which forms said cavities so that said sample solution is movable in said cavities;

subjecting a substitution solution to a degassing treatment;

charging said substitution solution into said cavities;

pouring different types of said sample solution into said pouring ports to effect substitution within each respective cavity; and driving said piezoelectric/electrostrictive elements so that mutually different types of said sample solution in said cavities are discharged from said discharge ports, wherein at least one sample solution is supplied onto the base plate a plurality of times to form one of said spots.

28. The method for producing said DNA chip according to claim 27, wherein said micropipettes are constructed such that said sample solution is moved in said cavities in a laminar flow.

29. The method for producing said DNA chip according to claim 27, wherein, when said sample solutions are supplied onto said base plate, said mutually different types of said sample solutions are poured into said cavities through said pouring ports corresponding to said discharge ports for discharging said mutually different types of said sample solutions, and then said mutually different types of said sample solutions in said cavities are discharged from said discharge ports by driving said piezoelectric/electrostrictive elements.

30. The method for producing said DNA chip according to claim 27, wherein said substitution solution is previously charged into said cavities, and said mutually different types of said sample solutions are poured into said pouring ports while effecting said substitution in said cavities, while driving said piezoelectric/electrostrictive elements.

31. The method for producing said DNA chip according to claim 27, wherein completion of pouring or substitution of said sample solutions in said cavities is recognized by sensing a change of a fluid characteristic in said cavities.

32. A method for producing a DNA chip including a large number of spots of at least one sample solution arranged on a base plate, said method comprising the steps of:

providing a dispenser comprising a plurality of arranged micropipettes each including a pouring port for pouring said sample solution from the outside, a cavity for pouring and charging said sample solution thereinto, and a discharge port for discharging said sample solution, formed on at least one substrate, said micropipettes comprising piezoelectric/electrostrictive elements disposed on at least one wall surface of said at least one substrate which forms said cavities so that said sample solution is movable in said cavities;

charging a substitution solution into said cavities;

pouring an intermediate solution containing no DNA fragments, which has approximately the same specific gravity as that of said sample solution, into said pouring ports while effecting substitution in said cavities;

pouring different types of said sample solution into said pouring ports to effect substitution within each respective cavity; and driving said piezoelectric/electrostrictive elements so that mutually different types of said sample solution in said cavities are discharged from said discharge ports, wherein at least one sample solution is supplied onto the base plate a plurality of times to form one of said spots.

33. The method for producing said DNA chip according to 32, wherein said micropipettes are constructed such that said sample solution is moved in said cavities in a laminar flow.

34. The method for producing said DNA chip according to 32, wherein, when said sample solutions are supplied onto said base plate, said mutually different types of said sample solutions are poured into said cavities through said pouring ports corresponding to said discharge ports for discharging said mutually different types of said sample solutions, and then said mutually different types of said sample solutions in said cavities are discharged from said discharge ports by driving said piezoelectric/electrostrictive elements.

35. The method for producing said DNA chip according to 32, wherein said substitution solution is previously charged into said cavities, and said mutually different types of said sample solutions are poured into said pouring ports while effecting said substitution in said cavities, while driving said piezoelectric/electrostrictive elements.

36. The method for producing said DNA chip according to 32, wherein completion of pouring or substitution of said sample solutions in said cavities is recognized by sensing a change of a fluid characteristic in said cavities.

37. A method for producing a DNA chip including a large number of spots of at least one sample solution arranged on a base plate, comprising the steps of:

supplying said sample solution onto the base plate a plurality of times to form one of said spots;

subsequently cooling said base plate to be not more than 0° C.; and returning said base plate to an atmosphere at room temperature in which a sufficient volume of gas exists at a humidity of not less than 30%.

38. A method for producing a DNA chip including a large number of spots of at least one sample solution arranged on a base plate, comprising the steps of:

supplying said sample solution onto the base plate a plurality of times to form one of said spots; and subsequently exposing said base plate in an atmosphere in which a sufficient volume of gas exists at a humidity of not less than 80%.

39. A method for producing a DNA chip including a large number of spots of at least one sample solution arranged on a base plate, comprising the steps of:

supplying said sample solution onto the base plate a plurality of times to form one of said spots; and subsequently exposing said base plate to a water vapor containing mist.

* * * * *